US008442651B2

(12) United States Patent
Martinez et al.

(10) Patent No.: US 8,442,651 B2
(45) Date of Patent: May 14, 2013

(54) MEDICAL DEVICE WITH SELF-HEALING MATERIAL

(75) Inventors: Gonzalo Martinez, Mendota Heights, MN (US); Jeffrey A. Wiser, Coon Rapids, MN (US); Gregory A. Boser, Richfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 283 days.

(21) Appl. No.: 12/718,897

(22) Filed: Mar. 5, 2010

(65) Prior Publication Data

US 2010/0312294 A1  Dec. 9, 2010

Related U.S. Application Data

(63) Continuation-in-part of application No. PCT/US2009/042136, filed on Apr. 29, 2009.

(60) Provisional application No. 61/049,335, filed on Apr. 30, 2008.

(51) Int. Cl.
*A61N 1/16* (2006.01)

(52) U.S. Cl.
USPC .......................................................... 607/116

(58) Field of Classification Search ........... 607/116–118
See application file for complete search history.

(56) References Cited

U.S. PATENT DOCUMENTS

| 3,239,731 A | 3/1966 | Matovich |
| 3,475,659 A | 10/1969 | Buice et al. |
| 3,813,549 A | 5/1974 | DeStefano et al. |
| 4,010,759 A * | 3/1977 | Boer ............................ 607/36 |
| 4,079,441 A | 3/1978 | Bush et al. |
| 5,384,544 A * | 1/1995 | Flugstad et al. ............ 324/678 |
| 5,455,736 A | 10/1995 | Nishiyama et al. |
| 6,072,694 A | 6/2000 | Hahn et al. |
| 6,191,013 B1 | 2/2001 | Hahn et al. |
| 6,212,055 B1 | 4/2001 | Lovkvist et al. |
| 6,518,330 B2 | 2/2003 | Moore et al. |
| 6,858,659 B2 | 2/2005 | White et al. |
| 6,944,489 B2 | 9/2005 | Zeijlemaker et al. |

(Continued)

FOREIGN PATENT DOCUMENTS

| WO | 03037424 A2 | 5/2003 |
| WO | WO 2008/036865 | 3/2008 |

(Continued)

OTHER PUBLICATIONS

Blaiszik et al., "Nanocapsules for self-healing materials," ScienceDirect, Composites Science and Technology 68, 2008, pp. 978-986.

(Continued)

*Primary Examiner* — Carl H Layno
*Assistant Examiner* — Paula J Stice
(74) *Attorney, Agent, or Firm* — Stephen W. Bauer; Michael J. Ostrom

(57) ABSTRACT

An electrode assembly for a medical device system includes an electrode, a shunted lead circuit, and a self-healing material integrated into the shunted lead circuit. The shunted lead circuit is designed to shunt currents induced by relatively high frequency radiation, such as MRI radiation. The self-healing material has a conductive layer and a dielectric layer, where the dielectric layer includes at least one of an oxide, an organic coating, and a composite.

38 Claims, 17 Drawing Sheets

U.S. PATENT DOCUMENTS

| | | |
|---|---|---|
| 6,985,775 B2 | 1/2006 | Reinke et al. |
| 7,174,219 B2 | 2/2007 | Wahlstrand et al. |
| 7,289,856 B1 | 10/2007 | Karicherla |
| 7,689,288 B2 | 3/2010 | Stevenson et al. |
| 7,751,903 B2 | 7/2010 | Stevenson et al. |
| 2002/0128691 A1 | 9/2002 | Connelly |
| 2003/0083723 A1 | 5/2003 | Wilkinson et al. |
| 2003/0216800 A1 | 11/2003 | Ebert et al. |
| 2004/0064175 A1* | 4/2004 | Lessar et al. .................. 607/122 |
| 2005/0070972 A1 | 3/2005 | Wahlstrand et al. |
| 2005/0090886 A1 | 4/2005 | MacDonald et al. |
| 2005/0159661 A1 | 7/2005 | Connelly et al. |
| 2006/0200218 A1 | 9/2006 | Wahlstrand |
| 2006/0205170 A1 | 9/2006 | Rinne |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2007/0093142 A1 | 4/2007 | MacDonald et al. |
| 2007/0208383 A1 | 9/2007 | Williams |
| 2007/0244535 A1 | 10/2007 | Inman et al. |
| 2007/0299490 A1 | 12/2007 | Yang et al. |
| 2008/0009905 A1 | 1/2008 | Zeijlemaker |
| 2008/0116997 A1 | 5/2008 | Dabney et al. |
| 2008/0132985 A1 | 6/2008 | Wedan et al. |
| 2008/0147154 A1 | 6/2008 | Gray et al. |
| 2008/0154346 A1 | 6/2008 | Smith et al. |
| 2008/0154348 A1 | 6/2008 | Atalar et al. |
| 2008/0221568 A1 | 9/2008 | Stone |
| 2008/0269830 A1 | 10/2008 | Marshall |
| 2008/0269855 A1 | 10/2008 | Marshall |
| 2008/0281390 A1 | 11/2008 | Marshall |
| 2009/0149920 A1 | 6/2009 | Li et al. |
| 2009/0149934 A1 | 6/2009 | Ameri et al. |
| 2009/0198314 A1 | 8/2009 | Foster et al. |
| 2009/0240296 A1 | 9/2009 | Zeijlemaker et al. |
| 2010/0217262 A1 | 8/2010 | Stevenson et al. |
| 2010/0312294 A1 | 12/2010 | Martinez et al. |
| 2011/0034979 A1 | 2/2011 | Min et al. |
| 2011/0040343 A1 | 2/2011 | Johnson et al. |
| 2011/0071604 A1 | 3/2011 | Wahlstrand et al. |

FOREIGN PATENT DOCUMENTS

| | | |
|---|---|---|
| WO | 2008095059 A1 | 8/2008 |
| WO | 2009134901 A1 | 11/2009 |
| WO | 2010008833 A1 | 1/2010 |

OTHER PUBLICATIONS

Brinker et al., "Evaporation-Induced Self-Assembly: Nanostructures Made Easy," Research News, Advanced Materials, Wiley-VCH, vol. 11, No. 7, 1999, pp. 579-585.

Kessler et al., "Self-healing structural composite materials," Science Direct, Composites Part A: applied science and manufacturing, 34, 2003, pp. 743-753.

Kessler et al., "Self-healing: a new paradigm in materials design," Special Issue Paper, JAERO172 IMechE 2007, Proc. IMechE vol. 221 Part G: J Aerospace Engineering, pp. 479-495.

Shchukin et al., "Layer-by-Layer Assembled Nanocontainers for Self-Healing Corrosion Protection," Advanced Materials, 2006, vol. 18, No. 3, pp. 1672-1678.

Shchukin et al., "Self-Repairing Coatings Containing Active Nanoreservoirs," www.small-journal.com, 2007, Wiley-VCH Verlag GmbH & Co. KGaA, Weinheim, vol. 3, No. 6, pp. 926-943.

Toohey et al., "Self-healing materials with microvascular networks," Nature Publish Group, vol. 6, No. 8, 2007, pp. 581-585.

Vasina et al., "Failure modes of tantalum capacitors made by different technologies," Pergamon; Microelectrics Reliability, 42, 2002, pp. 849-854.

White et al., "Autonomic healing of polymer composites," 2001 Macmillian Magazines Ltd., Nature, vol. 409, Feb. 15, 2001, pp. 794-797.

Wu et al., "Self-healing polymeric materials: A review of recent developments," ScienceDirect, Progress in Polymer Science, Pergamon Press, vol. 33, No. 5, 2008, pp. 479-522.

International Search Report and Written Opinion for PCT/US2009/042136, mail date Oct. 13, 2009, 20 pages.

Stream Chemicals, Layer-by Layer Assembled Nanocontainers as Corrosion Inhibitors, Advanced Materials 2006, 18, No. 13, 4 pgs.

Ghosh, Self-healing Materials: Fundamentals, Design Strategies and Application, Wiley-VCH, Jan. 20, 2009, pp. 101-139.

\* cited by examiner

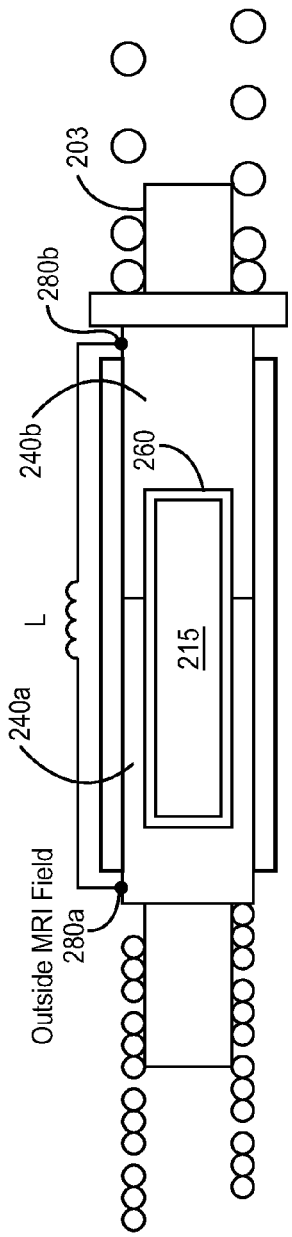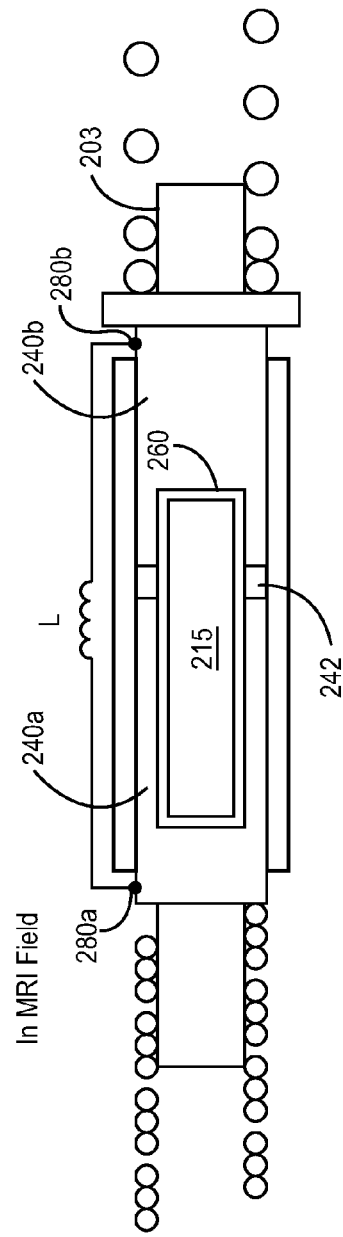

MEDICAL DEVICE WITH SELF-HEALING MATERIAL

CROSS-REFERENCE TO RELATED PATENT APPLICATIONS

This application is a continuation-in-part of International Application No. PCT/US2009/042136, filed Apr. 29, 2009, which claims the benefit of U.S. Provisional Application No. 61/049,335, filed Apr. 30, 2008. International Application No. PCT/US2009/042136 and U.S. Provisional Application No. 61/049,335 are incorporated herein by reference in their entireties.

TECHNICAL FIELD

The invention relates to medical devices and, more particularly, to self-healing components of medical devices, such as leads, electrodes, capacitors, protective coatings and insulation for use with implantable medical devices (IMDs).

BACKGROUND

In the medical field, implantable leads are used with a wide variety of medical devices. For example, implantable leads are commonly used to form part of implantable cardiac pacemakers that provide therapeutic stimulation to the heart by delivering pacing, cardioversion or defibrillation pulses. The pulses can be delivered to the heart via electrodes disposed on the leads, e.g., typically near distal ends of the leads. In that case, the leads may be used to position the electrodes with respect to various cardiac locations so that the pacemaker can deliver pulses to the appropriate locations. Leads are also used for sensing purposes, or for both sensing and stimulation purposes. Implantable leads are also used in neurological devices, muscular stimulation therapy, and devices that sense chemical conditions in a patient's blood or gastric system stimulators.

Another type of IMD is an implantable neurological stimulation device (sometimes referred to as an implantable neurostimulator or INS). INS devices can generate electrical stimulation signals that are used to influence the human nervous system or organs. Conventionally, the INS devices have been surgically implanted into a patient in a subcutaneous pocket in the abdomen, pectoral region, or upper buttocks area. Electrical contacts carried on the distal end of a lead are placed at the desired stimulation site (e.g., at a location in the spine or directly in the brain) and the proximal end of the lead is connected to the INS. The lead typically has one or more insulated electrical conductors (filers) that connect the electrical contacts, or electrodes, to the INS. For neurostimulation of the spine or brain, the leads may typically have 4 or 8 sets of conductors and electrodes.

It may be desirable to implant the INS at a location in the patient's head in cases where the distal end of the lead is provided at a site directly in the brain. For example, it may be desirable to implant the INS under the scalp on top of the patient's head (either on top of the surface of the skull or in a pocket formed in the skull).

Deep brain stimulation implants may be used for the treatment of a variety of diseases including epilepsy and Parkinson's Disease. In these devices, the electrodes are implanted in the brain of the patient to provide electric stimulation to affected regions of the brain.

Alternatively, the leads may be placed in the epidural region of the spine to stimulate the dorsal horn of the spinal cord for the treatment of pain, or other diseases such as angina.

Occasionally, patients that have implantable leads may benefit from a magnet resonance image (MRI) being taken of a particular area of his or her body, such as to monitor a disease or to diagnose an unrelated injury or disorder. MRI systems use radio frequency radiation in the presence of a strong magnetic field to produce diagnostic images of the patient. MRI techniques can achieve an effective image of the soft tissues of the heart and vascular system. MRI procedures can also image these features without delivering a high dosage of radiation to the body of the patient, and as a result, MRI procedures may be repeated reliably and safely. However, MRI devices may operate at frequencies of 10 megahertz or higher, which may cause energy to be transferred to the lead and can produce a voltage that can interact with surrounding tissue.

SUMMARY

One embodiment of the invention relates to an electrode assembly for a medical device system. The electrode assembly includes an electrode, a shunted lead circuit, and a self-healing material integrated into the shunted lead circuit. The shunted lead circuit is designed to shunt currents induced by relatively high frequency radiation, such as MRI radiation. The self-healing material has a conductive layer and a dielectric layer, where the dielectric layer includes at least one of an oxide, an organic coating, and a composite.

Another embodiment of the invention relates to a medical device system. The medical device system includes a medical device and a lead. The medical device is adapted to provide an electrical stimulation to a patient. The lead is electrically connected to the medical device, and includes at least one electrode assembly. The electrode assembly includes an electrode and a shunted lead circuit. The lead includes a self-healing material integrated onto a surface of at least a portion of the lead. The medical device system is designed to control the regeneration rate of the self-healing material.

Yet another embodiment of the invention relates to a medical device system. The medical device system includes an implantable medical device, an electrical lead, and a self-healing material. The implantable medical device has a housing adapted to be implanted within a body of a patient. The electrical lead includes an electrode and is connected to the implantable medical device. The electrode is adapted to perform at least one of sensing electrical activity of an organ of the patient, and delivering an electrical stimulation to the organ of the patient. The self-healing material is attached to at least one of the implantable medical device and the electrical lead, and is designed to repair a breach while implanted within the body of the patent.

Still another embodiment of the invention relates to a method for making a medical device system having regenerative capabilities. The method includes a step of providing an implantable medical device adapted to be implanted within a body of a patient. The method includes another step of providing an electrical lead connected to the implantable medical device. The electrical lead is adapted to perform at least one of sensing electrical activity of an organ of the patient, and delivering an electrical stimulation to the organ of the patient. The method includes yet another step of providing an electrical circuit to electrically connect the implantable medical device and the electrical lead. The method includes still another step of providing in the electrical circuit a dielectric material that is designed to be regenerated while implanted within the body of the patient.

Another embodiment of the invention relates to a method for using a medical device system having regenerative capabilities. The method includes a step of providing a medical device having an electrical circuit to electrically connect the medical device and an electrical lead. The electrical lead is adapted to perform at least one of sensing electrical activity of an organ of a patient, and delivering an electrical stimulation to the organ of the patient. The electrical circuit includes a dielectric material that is designed to be regenerated while implanted within a body of the patient. The method includes yet another step of implanting the medical device into the body of the patient. The method includes still another step of connecting the electrical lead to the organ of the patient.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein:

FIG. 7A depicts a cross-sectional view of an electrode assembly with a magnetostrictive element integrated into the electrical circuit for the electrode.

FIG. 7B depicts a cross-sectional view of an electrode assembly with a magnetostrictive element integrated into the electrical circuit for the electrode wherein an open circuit condition exists.

DETAILED DESCRIPTION

Figure 1:
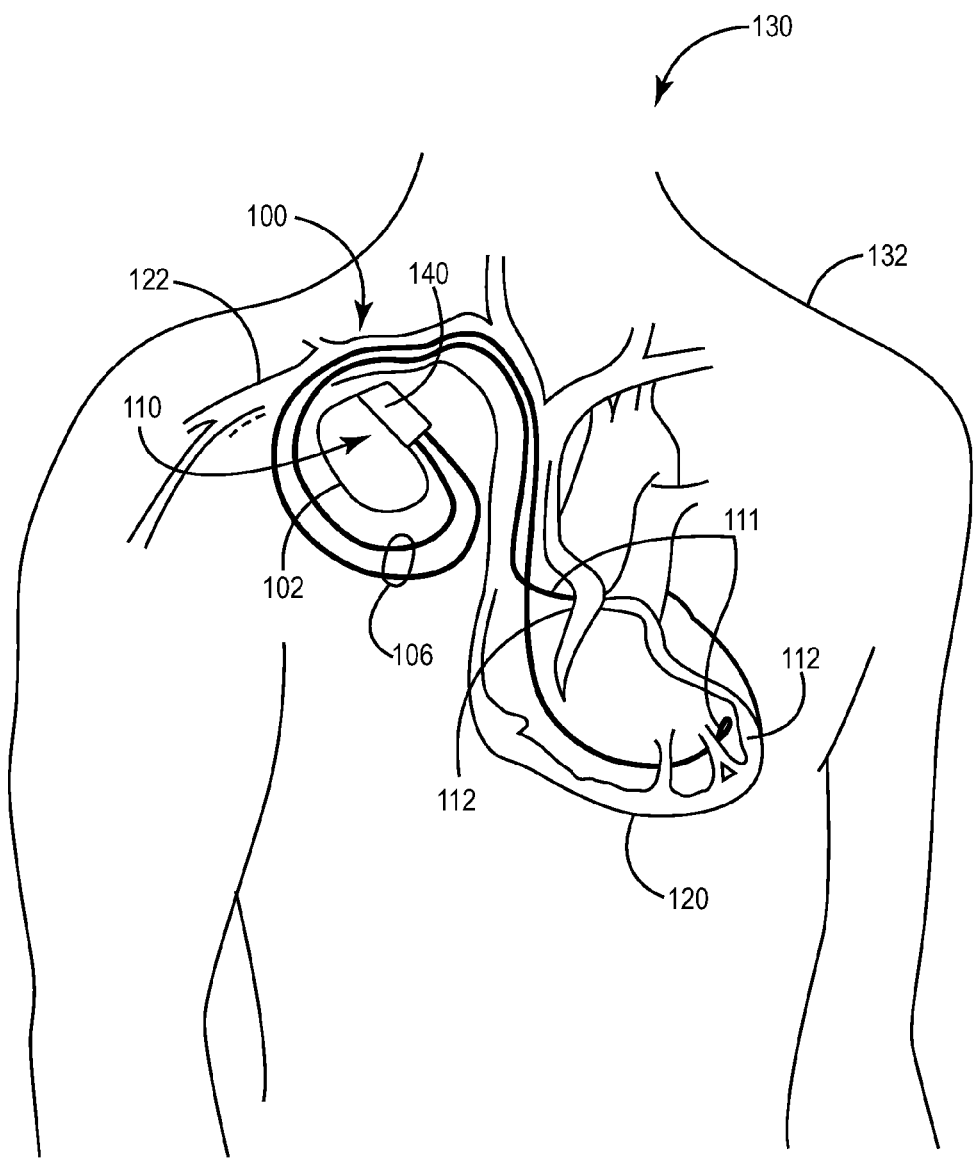
FIG. 1 is a schematic view of an implantable medical device placed in a human body.
Figure 2:
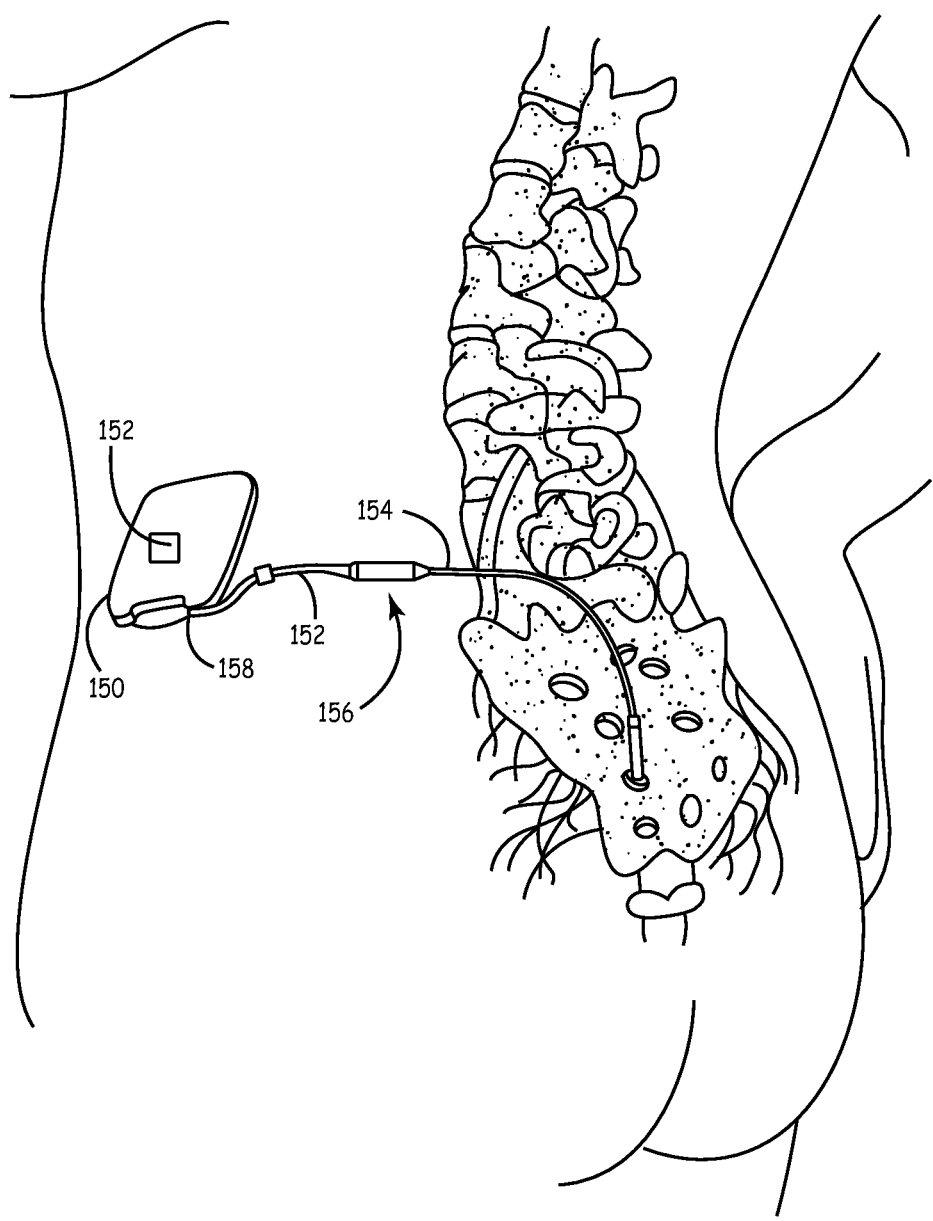
FIG. 2 is a schematic view of another implantable medical device placed in a human body.

Throughout the present disclosure various medical device systems (e.g., system 100 as shown in FIG. 1, device 150 as shown in FIG. 2, etc.) are presented, providing a range of context and background relevant to the disclosure. For example, some embodiments of the present invention are directed to a medical lead, techniques for manufacturing such a lead, and systems that include a medical device coupled to a medical lead according to the present invention. However the medical lead, and other exemplary systems and devices shown in the FIGURES, are only some of the many devices and systems to which the present disclosure may apply.

FIG. 1 illustrates a schematic view of a medical device system 100 (e.g., an implantable medical device or IMD) implanted within a body or torso 132 of a patient 130. The medical device system 100 may include electrodes having thermally and/or magnetorestrictive sensitive switches. The medical device system 100 includes a device 110 in the form of an implantable medical device that for purposes of illustration is shown as a defibrillator configured to provide a therapeutic high voltage (e.g., 700 volt) treatment for the patient 130.

The device 110 includes a container or housing 102 that is hermetically sealed and biologically inert according to an exemplary embodiment. The container may be made of a conductive material. One or more leads 106 electrically connect the device 110 to an organ or tissue such as the patient's heart 120 via a vein 122. Electrodes are provided to sense cardiac activity of the organ or tissue and/or provide an electrical potential to the organ or tissue such as the heart 120. At least a portion of the leads 106 (e.g., an end portion of the leads shown as exposed electrodes 111 attached to heart tissue 112) may be provided adjacent or in contact with one or more of a ventricle and an atrium of the heart 120.

The device 110 includes a battery 140 provided therein to provide power for the device 110. The size and capacity of the battery 140 may be chosen based on a number of factors, including the amount of charge required for a given patient's physical or medical characteristics, the size or configuration of the device, and any of a variety of other factors. According to an exemplary embodiment, the battery is a 5 mAh battery. According to another exemplary embodiment, the battery is a 300 mAh battery. According to various other exemplary embodiments, the battery may have a capacity of between approximately 10 and 1000 mAh.

According to another exemplary embodiment shown in FIG. 2, an implantable neurological stimulation device 150 (an implantable neurostimulator or INS) may include a battery 162 such as those described above with respect to the various exemplary embodiments. Examples of some neurostimulation products and related components are shown and described in a brochure titled "Implantable Neurostimulation Systems" available from Medtronic, Inc.

An INS generates one or more electrical stimulation signals that are used to influence the human nervous system or organs. Electrical contacts carried on the distal end of a lead are placed at the desired stimulation site such as the spine or brain and the proximal end of the lead is connected to the INS. The INS is then surgically implanted into an individual such as into a subcutaneous pocket in the abdomen, pectoral region, or upper buttocks area. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea. Additional therapies appear promising to treat a variety of physiological, psychological, and emotional conditions.

The INS 150 typically includes a lead extension 152 and a stimulation lead 154. The stimulation lead 154 is one or more insulated electrical conductors with a connector 156 on the proximal end and electrical contacts (not shown) on the distal end. Some stimulation leads are designed to be inserted into a patient percutaneously, such as the Model 3487A Pisces-Quad® lead available from Medtronic, Inc. of Minneapolis Minn., and some stimulation leads are designed to be surgically implanted, such as the Model 3998 Specify® lead also available from Medtronic. Although the lead connector 156 can be connected directly to the INS 150 (e.g., at a point 158), typically the lead connector 156 is connected to a lead extension 152. The lead extension 152, such as a Model 7495 available from Medtronic, is then connected to the INS 150. Implantation of an INS 150 typically begins with implantation of at least one stimulation lead 154, usually while the patient is under a local anesthetic. The stimulation lead 154 can either be percutaneously or surgically implanted. Once the stimulation lead 154 has been implanted and positioned, the stimulation lead's 154 distal end is typically anchored into position to minimize movement of the stimulation lead 154 after implantation. The stimulation lead's 154 proximal end can be configured to connect to a lead extension 152. The INS 150 is programmed with a therapy and the therapy is often modified to optimize the therapy for the patient (i.e., the INS may be programmed with a plurality of programs or therapies such that an appropriate therapy may be administered in a given situation).

According to an embodiment, a medical device lead includes a lead body, and electrode shaft and a tip electrode. A magnetostrictive element, coupled to an electrode shaft, serves as an "on/off" switch to manage high frequency RF signals (e.g. 21 megaHertz (Mhz) to 128 MHz) generated from a magnetic resonance imaging (MRI) machine away from the tip electrode. The switch is comprised of a magnetostrictive element made of any suitable material with sufficient magnetostrictive properties. Exemplary magnetostrictive materials include terfenol-D or galfenol. Magnetostriction is a property that causes certain ferromagnetic materials to change shape in response to a magnetic field. In particular, the magnetostrictive element expands or contracts. When the lead is not exposed to magnetic resonance imaging (MRI), the magnetostrictive material is contracted. In contrast, when the lead is exposed to MRI, the magnetostrictive material expands. In one embodiment, expansion of the magnetostrictive material causes a first segment to move away from a second segment of the electrode shaft. A gap is created between the first and second segments of the electrode shaft. Therefore, current, induced in the lead due to exposure to the MRI, no longer has a direct electrical path to the tip electrode. Instead, the electrical current induced by high frequency passes through a high impedance component such as a radiofrequency (RF) trap, whereas the low frequency current for sensing and/or pacing is able to pass to and/or from the electrode tip. Consequently, a patient with a medical lead may undergo an MRI procedure without significantly affecting the operation of the medical lead.

In another embodiment, magnetostrictive material is disposed in or near conductive members that are coupled to the electrode shaft. When the lead is exposed to MRI, the magnetostrictive material expands to create a contact to an additional electrode surface, which allows the induced current to dissipate over a larger surface area. In one embodiment, a tenfold (i.e. 10×) larger surface area ratio results in about tenfold lower temperatures at the tip electrode, assuming a ring electrode has low impedance at high frequencies. The principles described herein are applicable to all types of medical electrical leads. For example, the disclosure applies to cardiovascular leads (e.g. high voltage leads, low voltage leads etc.), neurological leads, or other suitable applications. Any size of lead can be used such as a size 13 French lead or less.

Figure 3:
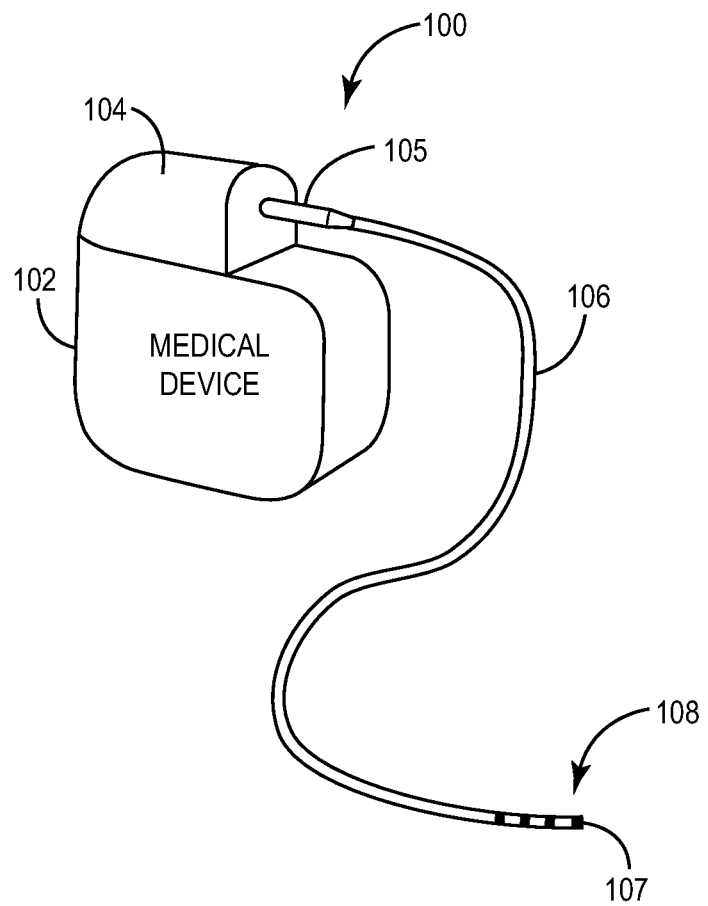
FIG. 3 is a conceptual perspective view of a medical device system including a medical device coupled to a lead according to an embodiment of the present invention.

FIG. 3 depicts a medical device system 100. According to an embodiment, a medical device system 100 includes a medical device housing 102 having a connector module 104 that electrically couples various internal electrical components of medical device housing 102 to a proximal end 105 of a medical lead 106. A medical device system 100 may comprise any of a wide variety of medical devices that include one or more medical lead(s) 106 and circuitry coupled to the medical lead(s) 106. An exemplary medical device system 100 may take the form of an implantable cardiac pacemaker, an implantable cardioverter, an implantable defibrillator, an implantable cardiac pacemaker-cardioverter-defibrillator (PCD), a neurostimulator, or a muscle stimulator. IMDs are implanted in a patient in an appropriate location. Exemplary IMDs are commercially available as including one generally known to those skilled in the art, such as the Medtronic CONCERTO®, SENSIA®, VIRTUOSO®, RESTORE®, RESTORE ULTRA®, sold by Medtronic, Inc. of Minnesota. Non-implantable medical devices or other types of devices may also utilize batteries such as external drug pumps, hearing aids and patient monitoring devices or other suitable devices. Medical device system 100 may deliver, for example, pacing, cardioversion or defibrillation pulses to a patient via electrodes disposed on distal ends 107 of one or more lead(s) 106. In other words, lead 106 may position one or more electrodes with respect to various cardiac locations so that medical device system 100 can deliver pulses to the appropriate locations.

Figure 4:
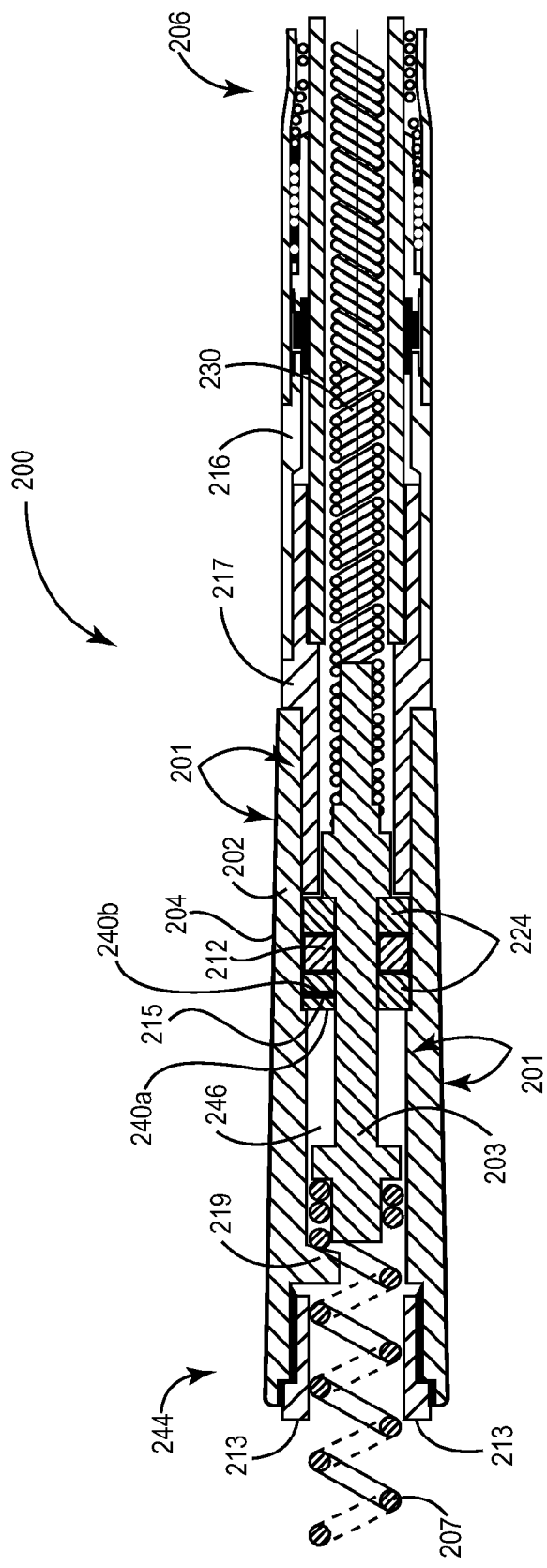
FIG. 4 is a cross-sectional view of one embodiment of an electrode assembly located at a distal end of a medical lead.

FIG. 4 depicts an electrode assembly 200 of a medical lead 106. Electrode assembly 200 senses physiologic data from a patient and/or delivers electrical stimuli to tissue of a patient. Electrode assembly 200 optionally includes a sleeve head 201 coupled to an electrode 207 (also referred to as a tip electrode), a monolithic controlled-release device (MCRD) 213, a conductive electrode shaft 203, a conductive sealer 212, conductive members 224, a ring electrode 216, and a non-conductive spacer 217. At a distal end 244 of electrode assembly 200, a sharpened distal tip (not shown) facilitates fixation of the distal end of helically shaped electrode 207 into tissue of a patient. The proximal end of electrode 207 is securely seated between MCRD 213, electrode shaft 203, and a securing member 219 that protrudes from an inner diameter of sleeve head 201. MCRD 213 provides chronic steroid elution to maintain a low pacing threshold for a medical device system 100.

Sleeve head 201 (optionally, a RF-shunted sleeve head) is electrically connected to a conductive electrode shaft 203 (e.g. platinum etc.) via two parallel conductive members 224 (e.g. C-rings etc.) a conductive sealer 212 (also referred to as a sealing washer), and a magnetostrictive element 215 insulated with insulative layer 260 (see, for example, FIGS. 7A and 7B). Insulative layer 260 is comprised of, for example, hydrolytically stable polyimide [commonly referred to as Langley Research Center SI ("LaRC SI") commercially available from Imitec located in Schenectady, N.Y.] Other insulative materials can also be used such as fluoropolymers [polytetrafluroethylene (PTFE), tetrafluroethylene (ETFE), etc.), thermoplastics [polyether ether ketone (PEEK), polyethersulfone (PES), etc.] and ceramic oxides (alumina, tantalum oxide, etc.). At a proximal end 206 of electrode assembly 200, coil 230 is electrically coupled to conductive electrode shaft 203. In another embodiment, electrode shaft 203 is made of nonconductive polymeric material.

Sleeve head 201 comprises a conductive element 202 surrounded or at least partially covered by an insulating material 204 (also referred to as a dielectric material). In one embodiment, conductive element 202 is cylindrically shaped (e.g. ring, etc.) or may possess other suitable shapes. Exemplary dimensions for conductive element 202 include a diameter of about 6.5 French (Fr.) by about 9 millimeters (mm) in length, an outer diameter of about 82 mils and an inner diameter of about 62 mils. Conductive element 202, in one embodiment, includes an increased diameter at the distal end and a reduced diameter at the proximal end of the conductive element 202. The surface area of conductive element 202 is about 60 mm$^2$ which is much larger than the 5.5 mm$^2$ surface area of electrode 207. Conductive element 202 comprises materials that are chemically stable, biocompatible, and x-ray transparent. Exemplary material used to form conductive element 202 includes tantalum, tantalum alloys, titanium, titanium alloy, conductive polymers, any combination these materials, and/or other suitable materials.

Figure 5:
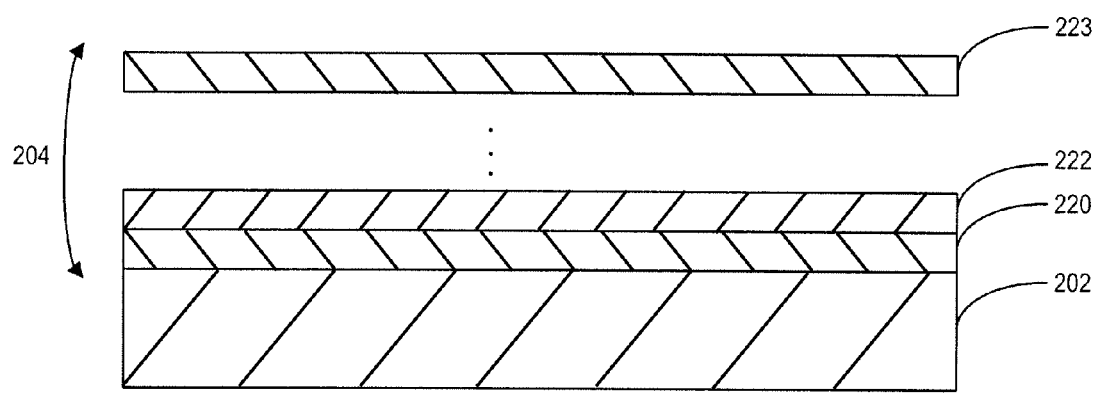
FIG. 5 depicts multiple layers of insulating material over a conductive element of the electrode assembly depicted in FIG. 4.
Figure 6A:
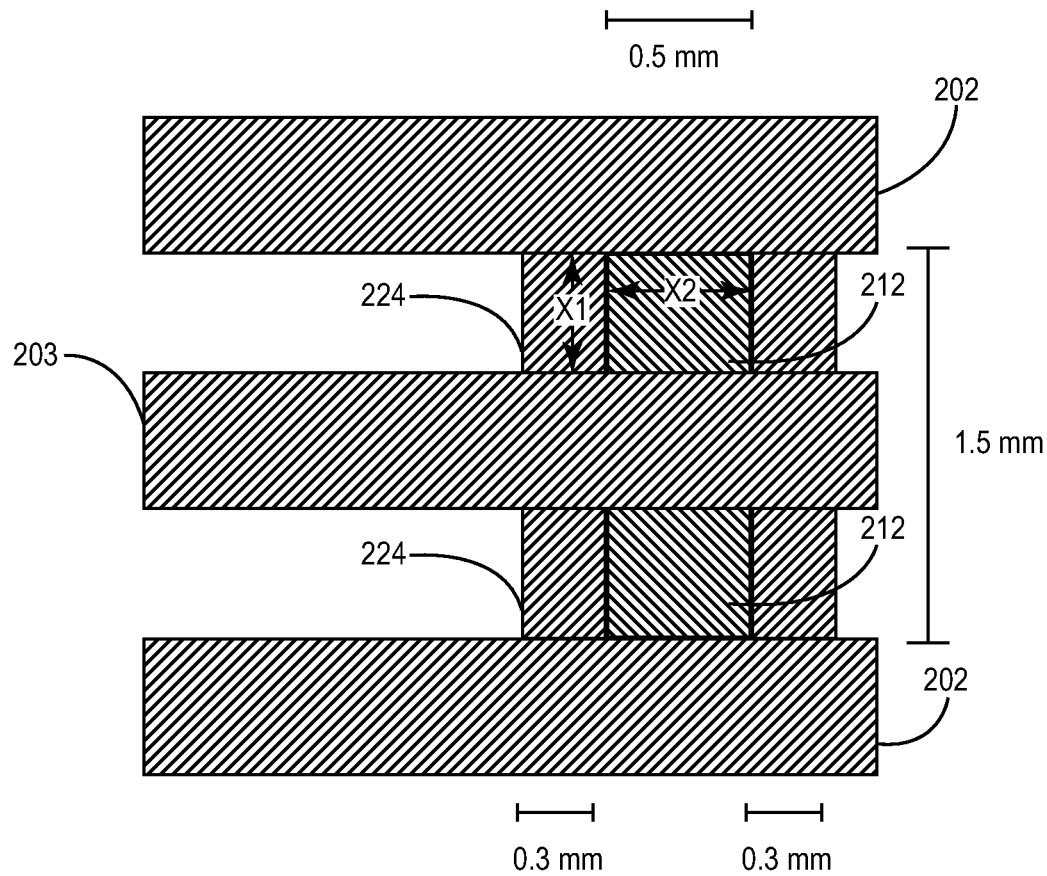
FIG. 6A depicts a cross-sectional view of a conductive ring coupled to a conductive sealer for the electrode assembly depicted in FIG. 4.
Figure 6B:
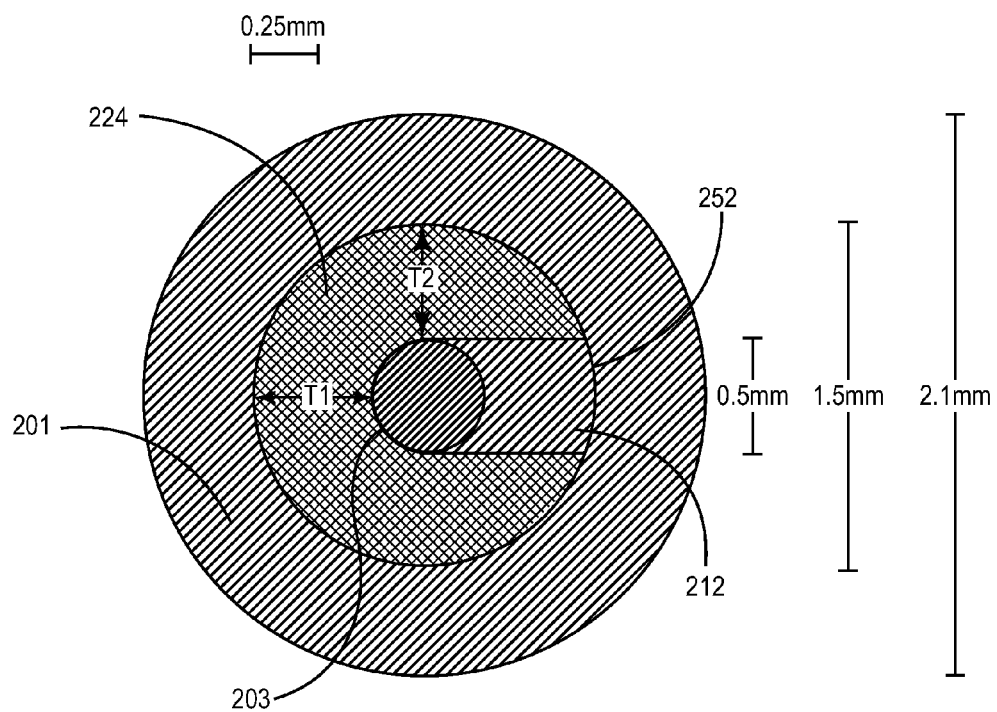
FIG. 6B depicts a top view of a conductive ring coupled to a conductive sealer for the electrode assembly depicted in FIG. 4.
Figure 6C:
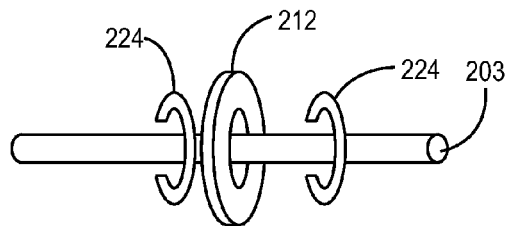
FIG. 6C depicts an exploded view of conductive members, specifically conductive rings and a conductive sealer coupled to a shaft.
Figure 6D:
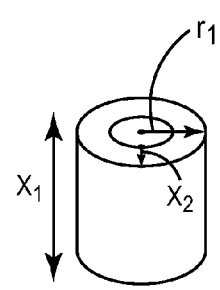
FIG. 6D depicts an angled view of a conductive sealer.

Referring to FIG. 5, insulative material 204 may be formed from a single layer or multiple layers such as first layer 220, second layer 222, and N layer 223, where N is a whole number that is less than 100, and is typically less than about 30 layers. Each layer may comprise different insulating materials, two or more different insulating materials, or the same insulating materials. Insulative material 204 includes a thickness from about 1 nanometer (nm) to about 1 millimeter (mm) and extends from about 1 mm to about 20 mm along the length of conductive element 202. Insulative material 204 may be formed from any of a wide variety of insulating materials. Exemplary insulating materials comprise at least one or more of parylene, polyamide, polyetheretherketone (PEEK), ceramics, ceramic composites, polymer composites, metal oxides, polyimide, urethane, silicone, tetrafluroethylene (ETFE), polytetrafluroethylene (PTFE), or the like. Parylene is a preferred insulating material 204. The preferred parylene is parylene C. Parylene C is formed through a dimer vacuum deposition process. The dimer is commercially available from Specialty Coating Systems located in Clear Lake, Wis. Numerous techniques may be employed to introduce insulating material 204 over the outside of sleeve head 201 and/or partially inside sleeve head 201. Exemplary techniques include physical vapor deposition, chemical vapor deposition, dip coating, spraying, electrophoretic deposition or thermal extrusion.

Conductive sealer 212 conducts current and also prevents fluid from passing through lumen 246. Referring to FIGS. 6A-6D, conductive sealer 212 is substantially ring (i.e. o-ring) or disk shaped but other suitable shapes may also be employed. In one embodiment, conductive sealer 212 is defined by X1, X2 and radius (r1). X1 can range from about 0.1 mm to about 0.50 mm, X2 can range from about 0.1 mm to about 1.0 mm, and r1 can range from about 0.5 mm to about 1.0 mm. Curved end 252 extends to about 1.25 mm from the center of shaft 203 and includes a curve defined by a radius of about 0.5 mm.

Conductive sealer 212 comprises a polymer and a conductive polymer such as a conductive powder (e.g. carbon, carbon nanotube, silver, platinum etc.). The conductive polymer can range from about 1% to about 25% of conductive sealer 212. The polymer (e.g. silicone etc.) is commercially available from Nusil Technology LLC, located in Carpinteria, Calif. Polyurethane is commercially available from The Polymer Technology Group Inc. located in Berkeley, Calif.

Conductive members 224 are shaped, in one embodiment, as a ring (e.g. C-ring, etc.) to receive conductive sealer 212. Conductive members 224 can have an outer diameter of about 1.5 mm, an inner diameter of about 0.7 mm, and a thickness that ranges from about 0.25 mm (T1) to about 0.5 mm (T2). Conductive members 224 can be comprised of platinum or other suitable materials.

In one embodiment, magnetostrictive element 215 is coupled to at least one conductive member 224, specifically a conductive ring. When lead 106 is exposed to MRI, magnetostrictive element 215 expands, which creates a larger surface area in which to dissipate the current induced in lead 106.

In another embodiment, as depicted in FIGS. 7A-7B, magnetostrictive element 215, is disposed between first and second segments 240a, 240b of electrode shaft 203. The magnetostrictive element 215 may be coated with an insulative material layer (such as polyimide) in a cylindrical shape of approximately 0.5 mm-2.0 mm in diameter by 1.0 mm-4.0 mm long and bonded at the ends of segment 240a, 240b. The outer surface of members 240a, 240b may also maintain contact through an elastic member assembled on the outside diameter. No gap exists between first and second segments 240a, 240b when MRI is not applied to lead 106, as shown in FIG. 7A. When lead 106 is exposed to MRI, magnetostrictive element 215 expands, causing first segment 240a to move away from second segment 240b, thereby creating a gap 242, as shown in FIG. 7B. Gap 242 breaks the direct electrical connection between first and second segments 240a, 240b and the tip electrode 207. Instead, the current induced by MRI is shunted to a RF trap. In particular, high impedance inductor (L) 262 connected to the electrode shaft 203, blocks the high frequency RF signals. L passes the low frequency pacing signals from one end 280a to another end 280b of the electrode shaft 203. Therefore, the high frequency RF signals experienced during MRI are shunted by the magnetostrictive element 215 as shown in FIG. 7B.

Figure 8A:
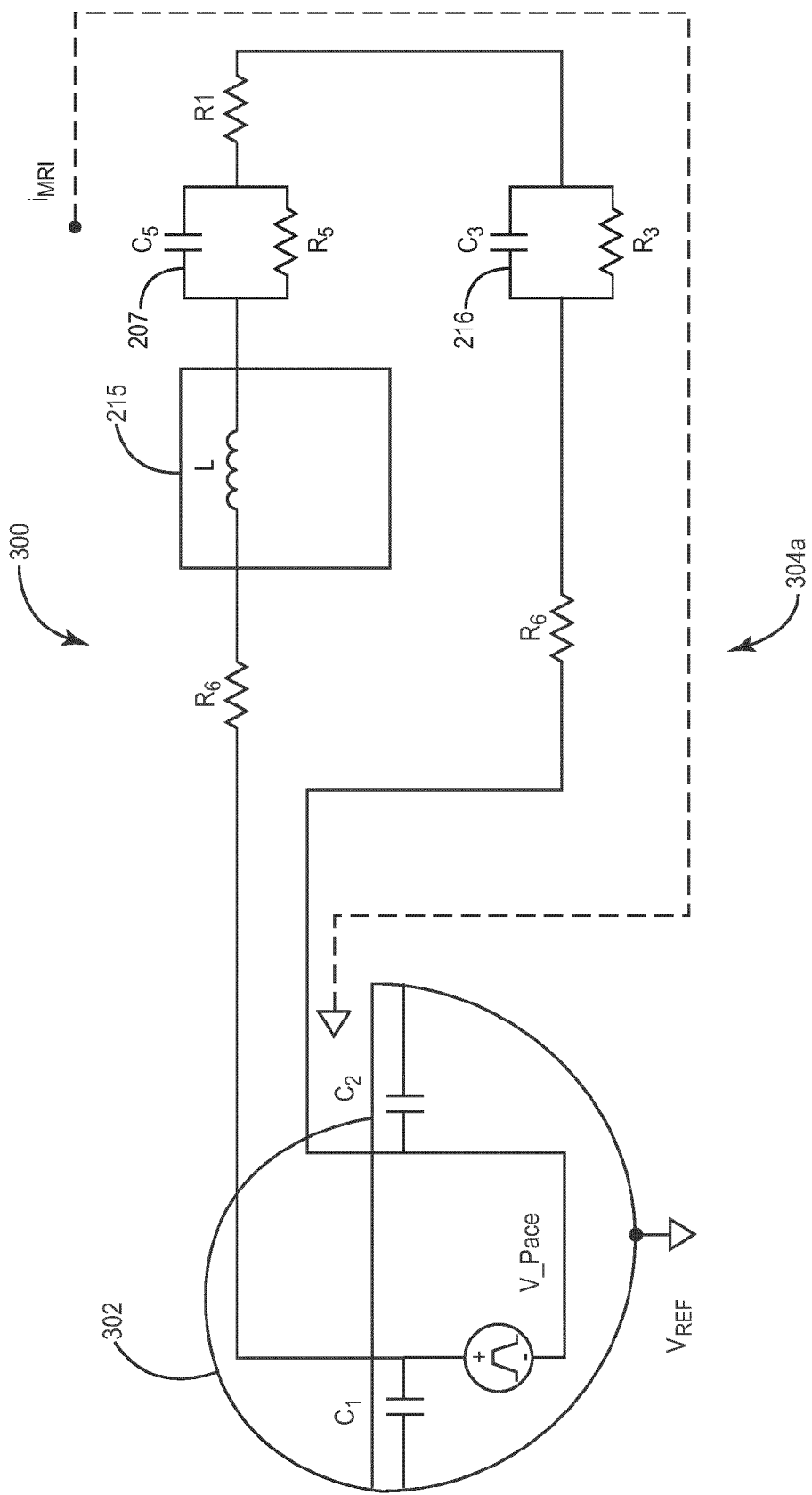
FIG. 8A is a schematic diagram of a simplified bipolar circuit for a medical device system under pacing and sensing conditions.

FIG. 8A depicts a simplified bipolar circuit 300 for a medical device system 100 during normal pacing conditions and when exposed to MRI. Pacing conditions typically involve low frequency signals (e.g. 1000 Hz). Circuit 300 includes an implantable medical device (IMD) circuit 302 (e.g. a pacemaker circuit, neurostimilator circuit etc.) connected to a bipolar shunted lead circuit 304a. IMD circuit 302 comprises two filter capacitors C1 and C2 connected to housing 102. C1 and C2 filter high frequency electromagnetic interference (EMI) so that high frequency signals from a MRI machine do not affect the sensing operation of medical lead 106. Exemplary values for C1 is about 1 to 10 nanoFarad (nF) and C2 is 1-10 nF.

Bipolar shunted lead circuit 304a includes ring electrode 216, magnetostrictive element 215, and tip electrode 207. Capacitors C3 and C5 correspond to ring electrode 216, and tip electrode 207, respectively and inductor L is associated with magnetostrictive element 215. Resistor R1 represents the impedance created by tissue and/or blood of the patient. R6 represents impedance or resistance associated with coil

230. R3 and R5, along with capacitors C3 and C5, represent the electrode to tissue interface impedances. $V_{REF}$ represents the device ground to the body whereas $V_{\_Pace}$ represents the voltage of the pacing current. Generally, larger area electrodes result in larger values of capacitance and smaller values of resistance. Exemplary values for bipolar shunted lead circuit 304a include L C3 at 10 microF (uF), L is 4 uHenry, R3 is 100 Ohm (Ω), C5 is 1 uF, and R1 is 500Ω, and R5 is Ω.

Bipolar shunted lead circuit 304a operates when the patient is not exposed to a MRI procedure or during a MRI procedure. When MRI conditions are not present and pacing pulses are required by a patient, pacing current is generated from C1 or C2 and passes through first and second segments 240a, 240b, as shown in greater detail in FIG. 7A. Thereafter, the pacing current passes through tip electrode 207, ring electrode 216 and back to medical device housing 102.

When a patient is exposed to a MRI procedure, a MRI current ($I_{MRI}$) is transferred from tip electrode 207 through ring electrode 216 back to medical device housing 102, which avoids or substantially prevents the MRI from affecting the operation of lead 106 from delivering electrical stimuli (i.e. pacing pulses) to the patient. If the patient requires pacing during the MRI, the pacing current, typically generated from C1, passes through an inductor (L), depicted in FIG. 7B, and thereafter passes through tip electrode 207, ring electrode 216 and then back to medical device housing 102.

Figure 8B:
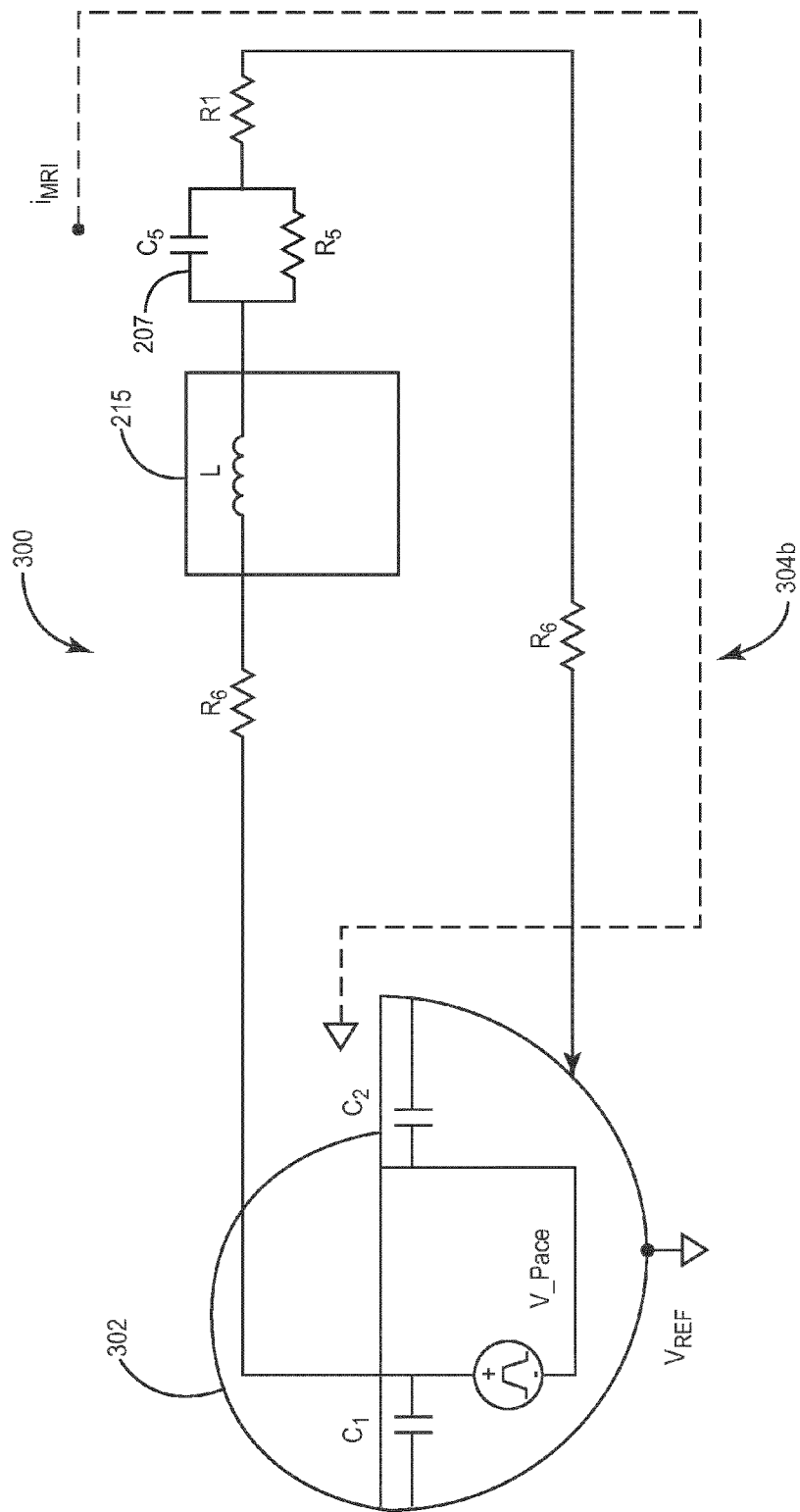
FIG. 8B is a schematic unipolar circuit for a medical device system.

FIG. 8B depicts a simplified unipolar circuit 300 for a medical device system 100 during normal pacing conditions and when exposed to MRI. Circuit 300 includes an IMD circuit 302 (e.g. a pacemaker circuit, neurostimulator circuit etc.) connected to a unipolar shunted lead circuit 304b. IMD circuit 302 comprises two filter capacitors C1 and C2 connected to housing 102. C1 and C2 filter high frequency EMI so that high frequency signals from a MRI machine do not affect the sensing operation of medical lead 106.

Unipolar shunted lead circuit 304b includes magnetostrictive element 215, and tip electrode 207. Capacitor C5 corresponds to tip electrode 207 and inductor L is associated with magnetostrictive element 215. Resistor R1 represents the impedance created by tissue and/or blood of the patient. R6 represents impedance or resistance associated with coil 230. R5 along with capacitor C5, represent the electrode to tissue interface impedance.

Generally, under typical pacing conditions, pacing current flows from C1 or C2 through tip electrode 207 and then returns to IMD circuit 302. Under a low frequency or DC application, inductor L acts like a short circuit to a constant voltage across its terminals. A portion of the pacing current passes to the patient's tissue (e.g. heart tissue), represented as resistor R1, due to the large capacitance of C5 associated with tip electrode 207. When lead 106 is exposed to MRI, $I_{MRI}$ is induced, as depicted by the ghost lines. As shown, the $I_{MRI}$ is transferred from tip electrode 207 back to medical device housing 102. If the patient requires pacing during an MRI procedure, a pacing current is generated from C1 or C2 and passes through inductor L, (shown in FIG. 8B), tip electrode 207 back to medical device housing 102.

Figure 9A:
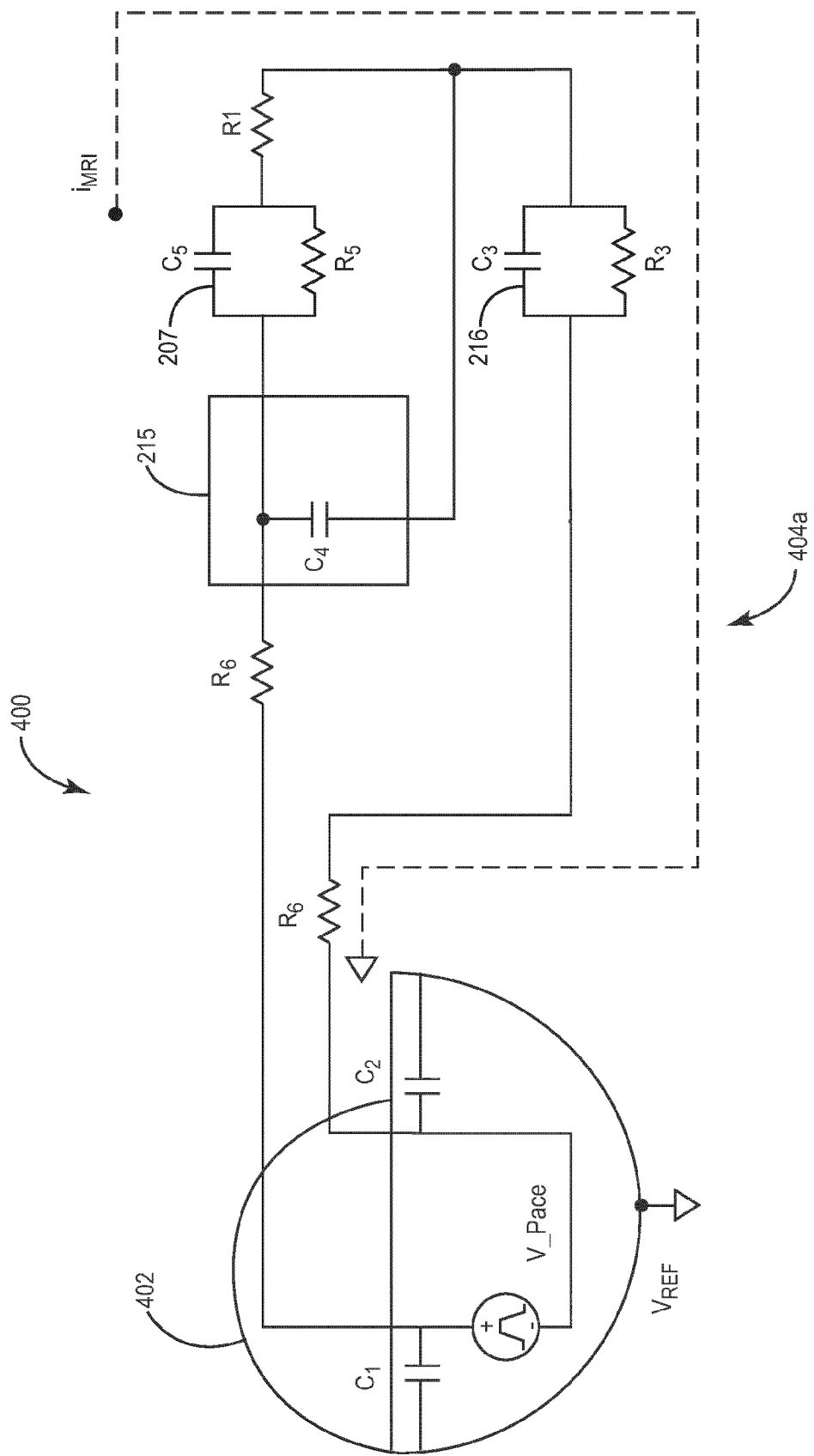
FIG. 9A is a schematic bipolar circuit for a simplified medical device system.
Figure 9B:
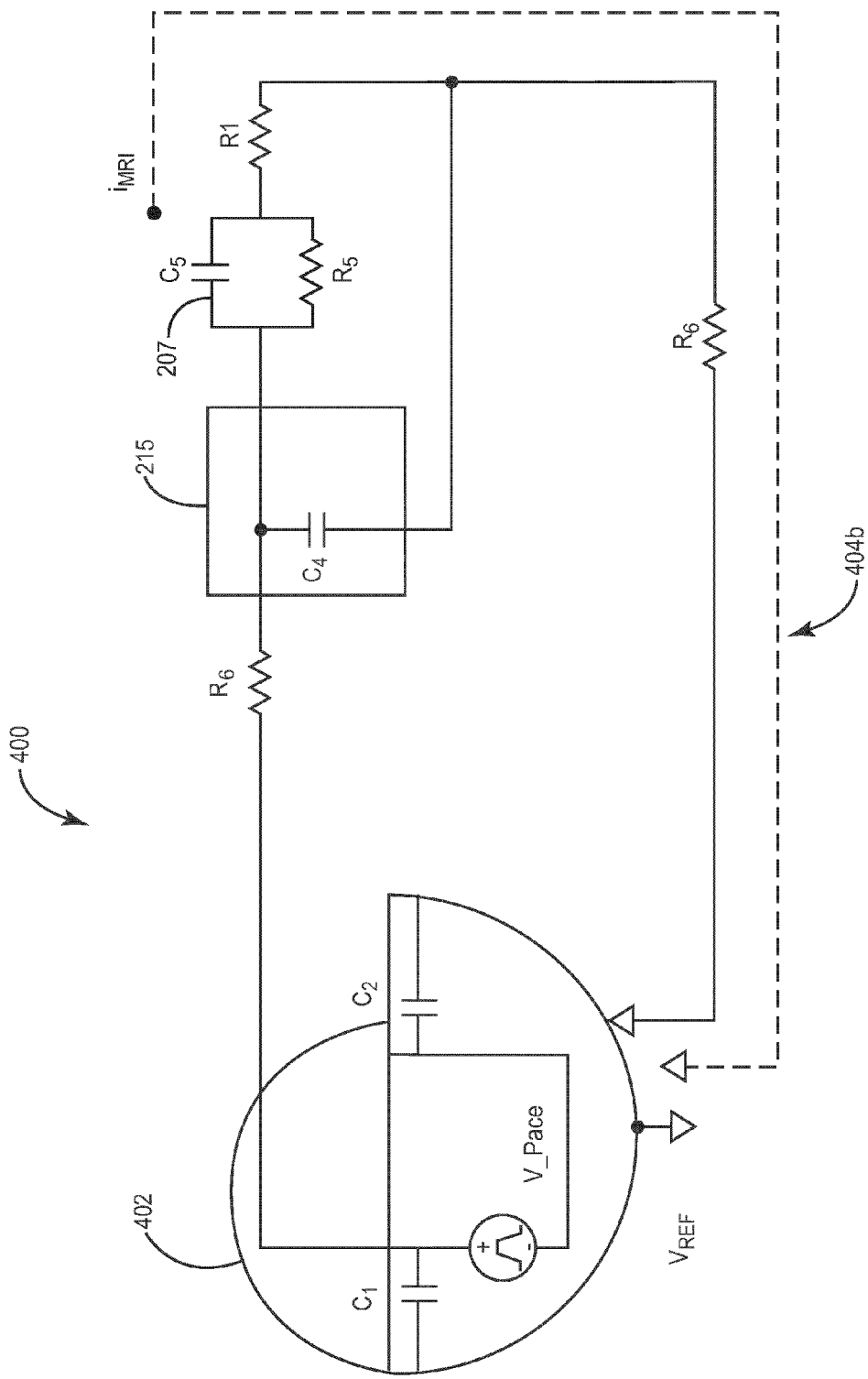
FIG. 9B is a schematic unipolar circuit for a simplified medical device system.

FIGS. 9A-9B depict another simplified circuit 400 for a medical device system 100 during pacing and MRI conditions, respectively. Referring to FIG. 9A, circuit 400 includes an IMD circuit 402 (e.g. a pacemaker circuit, neurostimulator circuit etc.) and a bipolar shunted lead 304b. Circuit 400 includes the same elements as circuit 300 depicted in FIG. 8A, except magnetostrictive element 215 is coupled to a capacitor (C4) instead of inductor L. Specifically, C4 serves to bypass first and second elements 240a, 240b when a patient undergoes a MRI procedure. Magnetostrictive material 215 only acts as a switch to turn on and off capacitor C4 in circuit 400. In this embodiment, high frequency signals (i.e. from the MRI) pass to C4, whereas low frequency signals pass to and from tip electrode 207. C4 is shorted when exposed to high frequency signals. C4 acts as an "open circuit" when exposed to low frequency signals, which causes the pacing pulses to pass directly to tip electrode 207. An exemplary value for C4 is about 1-10 uF. For the bipolar shunted lead circuit 404a depicted in FIG. 9A, $i_{MRI}$ is transferred from tip electrode 207 through ring electrode 216 back to medical device housing 102, which avoids or substantially prevents the MRI from affecting the operation of lead 106 from delivering electrical stimuli (i.e. pacing pulses) to the patient.

Figure 10:
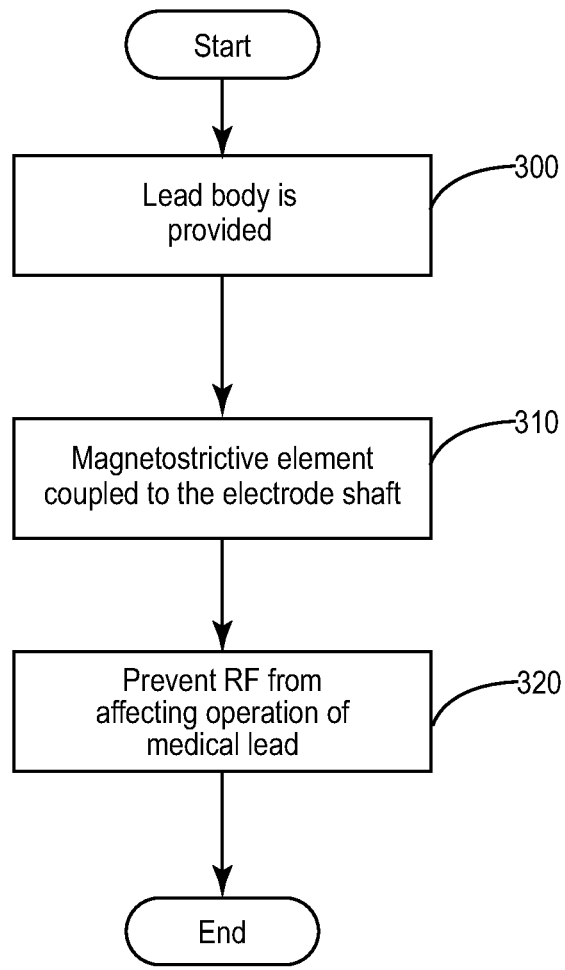
FIG. 10 is a flow diagram that depicts the method of producing an electrode assembly.

FIG. 10 is a flow diagram that depicts a method of producing a medical lead. At block 300, a lead body is provided. At block 310, a magnetostrictive element is inserted or placed between a lead body and an electrode shaft. The magnetostrictive element is comprised of a ferromagnetic material (e.g. terfenol-D, galfenol etc.), commercially available from Extrema Products Inc. located in Ames, Iowa. Terfenol-D, an alloy of terbium, dysprosium, and iron metals with the formula of terbium (Tb)(0.3) dysprosium (Dy)(0.7) iron (Fe) (1.9), was developed at the Naval Ordnance Laboratory in America. Generally, terfenol has the largest room temperature magnetostriction of any material. In mechanical terms, a 2.5 inch diameter rod of terfenol-D is capable of generating over 50,000 pounds of dynamic force. In one embodiment, the magnetostrictive element can comprise one or more terfenol-D or galfenol. In another embodiment, the magnetostrictive element can comprise terfenol-D and/or galfenol in combination with other suitable materials.

At block 320, the RF is prevented from affecting the sensing operation of the medical lead. In one embodiment, the magnetostrictive element reduces by at least 80 percent the current, induced in the lead by the MRI. In another embodiment, the magnetostrictive element reduces by at least 50 percent the current induced by the MRI.

A possible issue with the use of materials that function as a capacitor to shunt energy induced in an electrode assembly, such as in the embodiments described above in regard to FIGS. 9A and 9B, is the performance of these materials after they have been implanted or during their use with a patient. For example, the materials forming a capacitor could suffer damage and such damage could diminish performance of the capacitor.

According to some embodiments, damage caused to components of medical devices, such as capacitors, insulations, conductors, electrodes, and other components, may be repaired or "healed" when "self-healing" materials are used to construct the components, or self-healing materials are provided in the form of protective coatings or layers upon the components. Some self-healing materials may be used to compensate for damage to component materials (e.g., materials of a capacitor of a medical device), because the self-healing materials can re-grow or regenerate (e.g., controlled oxidation, corrosion, chemical reaction, etc.) upon a damaged area, thus fixing, mending, healing, or reducing damage caused to the component materials. Other self-healing materials can migrate or chemically diffuse to a damaged area and subsequently harden, thus repairing the damage caused to the capacitor, or other component. According to an exemplary embodiment, the self-healing materials may regenerate or self-heal while in service, such as while implanted within or on a patient.

Figure 11A:
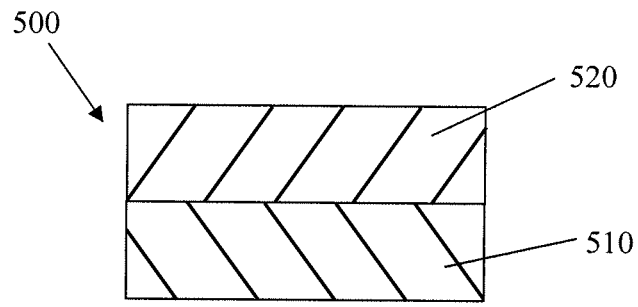
FIG. 11A is a cross-sectional view of materials that form a capacitor.

FIG. 11A shows an embodiment of a component of a medical device, such as a shunt capacitor 500 that includes a conducting layer 510 and a dielectric layer 520. In some embodiments, the capacitor 500 may be connected to another conductor, providing an additional conductor on the opposite side of the dielectric material 520 to conductor 510 (or otherwise coupled to the dielectric material 520). For example, a conductive component of an electrode assembly 200, such as a ring electrode 216, may be connected to the capacitor 500 to provide an additional conductor. According to a further embodiment, the dielectric layer 520 is an exterior layer of an electrode assembly 200 and is formed of a material that is biocompatible, and an additional conductor may be connected to the dielectric layer 520. According to a further embodiment, the conducting layer 510 and the dielectric layer 520 may be applied as coating layers to an electrode assembly of a medical device system. In some embodiments, self-healing materials may be used to enhance the performance, durability, and usable life of the shunt capacitor 500, or other medical system, device, or component.

Figure 11B:
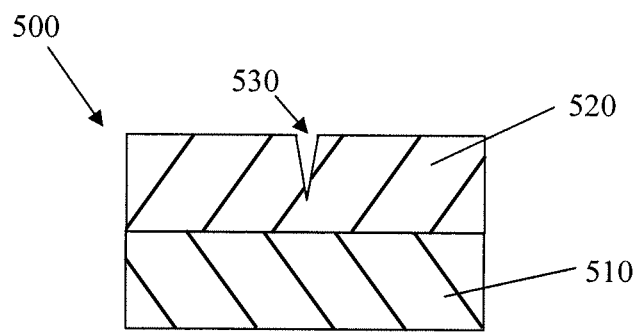
FIG. 11B is a cross-sectional view of materials that form a capacitor, whereby one of the materials is damaged.

FIG. 11B shows the capacitor 500 in a state in which the dielectric layer 520 has sustained damage 530. Damage 530 could have been sustained for any of a variety of reasons for example, during implantation or use of the electrode for which the capacitor 500 is associated. Damage 530 could occur in one or more of many forms including scratches, gouges, dents, cracks or other forms of damage that can occur to capacitor materials and coatings for such materials. Such damage 530 can be problematic to the performance of the capacitor 500.

Figure 11C:
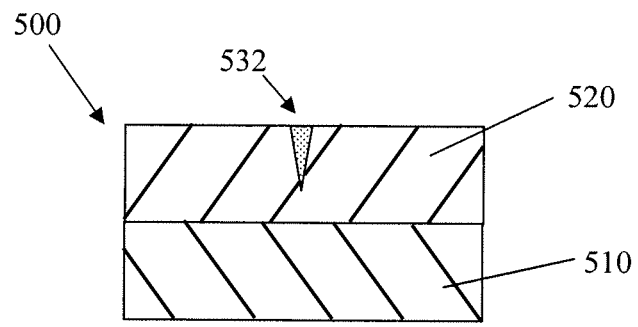
FIG. 11C is a cross-sectional view of materials that form a capacitor, whereby the damage to one of the materials has been repaired or healed.

FIG. 11C shows a capacitor 500 that has regenerated or re-grown material 532 to heal damage caused to the dielectric layer 520 of the capacitor 500. Regenerated or re-grown material 532 may be created through the use of self-healing capacitor materials for the conductor 510 and/or the dielectric 520. This re-growth or "healing" operation reduces damage to the dielectric layer. In other embodiments, re-growth or healing operations reduce damage to a biocompatible layer, a fracture-resistant layer (e.g., formed with a material having a high toughness), a thermally-insulating layer, a structural reinforcement layer, or other layers performing other functions.

In other exemplary embodiments, a layer of polymer insulation may be coupled to a conducting layer within a medical device, or other device. Depending upon the particular application and use, the layer of polymer insulation may be susceptible to various modes of failure. For example, typical failure modes for polymer insulation layers include chemical instability or degradation (e.g., metal ion oxidation (MIO), environmental stress cracking (ESC) with polyurethanes, etc.), abrasive wear, adhesive wear, cold-flow or creep under compression or other loading conditions, cyclic fatigue with bending, compression, or other loads, and various processing conditions that may affect the integrity of the polymer materials, such as phase separations, gels or other discontinuities, pin-holes, sub-optimal chemical, physical, mechanical, or electrical properties, etc.

Referring back to FIGS. 1-3 and in other embodiments, electrical leads for medical devices may be used to stimulate systems of the body or to sense bodily activity (see, e.g., lead 106 as shown in FIG. 1). Such electrical leads may be employed for defibrillation (see, e.g., medical device system 100 as shown in FIG. 1), neurological stimulation (see, e.g., medical device system 150 as shown in FIG. 2), heart pacing, cardiac resynchronization therapy (CRT), etc. There is the possibility that electrical leads may fail via various modes, and as such, the electrical leads benefit from construction with redundant or self-healing materials. For example, modes of potential failure for conductors employed by electrical leads include overstress (e.g., during torquing of a coil to extend a fixation helix in a screw-in lead), low and high-cycle fatigue under bending, excessive compressive or tensile loading conditions, corrosion, weld/crimp joint failure, etc.

While FIG. 11A shows a conducting layer 510 and a dielectric layer 520 for a capacitor 500, layers of materials may be similarly arranged and used with other medical device systems and components. In some embodiments, electrical leads of medical devices include layers of materials, such as a regenerative insulator layer and a regenerative conductive layer. In other embodiments, housings or casings for implantable medical devices may include an insulator layer and a structural layer, a protective coating and a conductive layer, a biocompatible layer and a thermal insulator layer, or other combinations of layers. In still other embodiments, layers may be configured in three-layer arrangements, four-layer arrangements, alternating striped layer arrangements, and other configurations of layers. In such arrangements, one or more of the layers may comprise regenerative or self-healing materials, where a scratched surface or breached layer may be re-sealed, healed, or repaired, for example.

Figure 12:
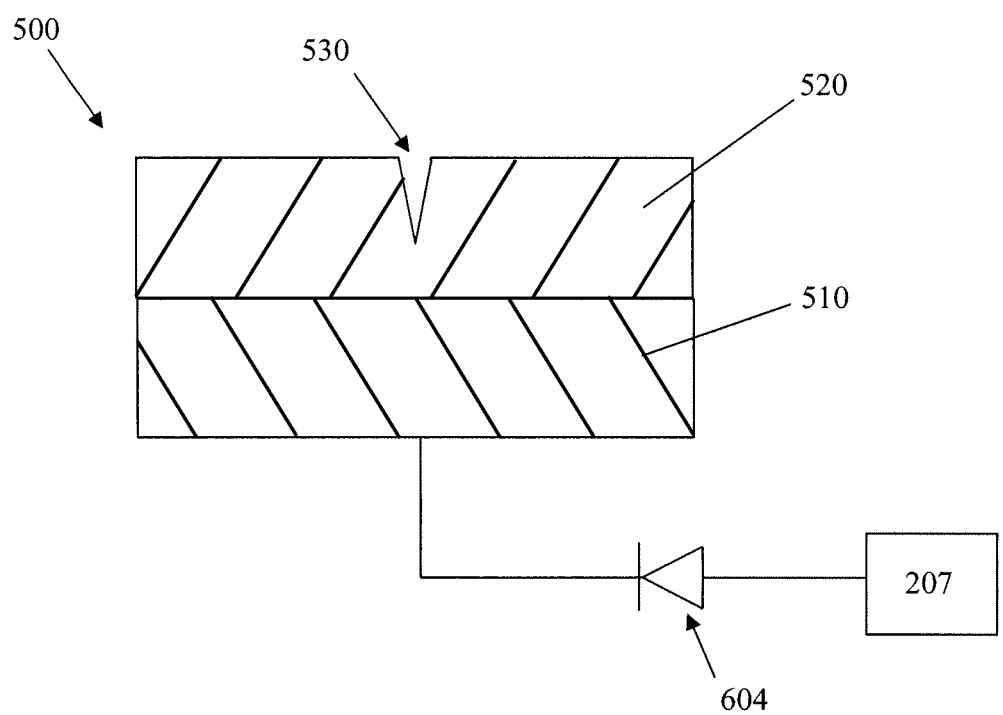
FIG. 12 is a schematic of a capacitor and diode arrangement.

Referring to FIGS. 11-12, according to an embodiment, the capacitor 500 includes a dielectric material 520 that may be regenerated or re-grown via anodization, passivation, or oxidation. For example, the dielectric material 520 can be regenerated or re-grown via anodization, passivation, or oxidation of the conductor 510. In some embodiments, a pulsed voltage filtered through a diode (positive or negative) facilitates the anodization, passivation, or oxidation processes in a material having an oxidized outer surface with an interior volume of a different phase or chemical composition, as will be further explained. In other embodiments, a biocompatible layer of a housing or structure of a medical device may be controllably regenerated or re-grown via anodization, passivation, or oxidation. In some applications, anodization, passivation, or oxidation allows for biocompatibility of an outer surface to be maintained, preventing unintended corrosion, unintended "tissue contact," weakening of materials, etc.

According to a further embodiment, the conductor 510 (or other component of a medical device) is formed from or made with an inorganic material. For example, the conductor 510 may be made of a metal and in particular, the conductor 510 can be made of a metal, such as, for example, tantalum, titanium, hafnium, yttrium, niobium, zinc, beryllium, aluminum, zirconium, tungsten, rhenium, and their alloys. According to one embodiment, the dielectric material 520, or other structure or layer, is made of an oxide corresponding to the material of the conductor 510, or other structure or layer. For example, the dielectric material 520 can be made of oxides, such as, for example, tantalum oxide, titanium oxide, hafnium oxide, yttrium oxide, zinc oxide, beryllium oxide, niobium oxide, aluminum oxide, zirconium oxide, tungsten oxide, rhenium oxide, and oxides of an alloy used for the conductor 510. In some embodiments, an electrical lead for a medical device includes a conductive substrate formed from tantalum, with tantalum oxide as an inorganic "self-healing" insulator material. Such an arrangement may "self-heal" after a breach to the tantalum core (i.e., substrate) by spontaneously forming a tantalum oxide layer.

In some exemplary embodiments, a conductor or electrode (see, e.g., electrodes discussed with regard to FIGS. 1-3) is formed from tantalum, tantalum oxide, or comprises a tantalum or tantalum oxide layer or coating. The tantalum or tantalum oxide layer may serve as a redundant insulation layer, and may also serve as a self-healing layer if the insulation layer were breached in service.

Fracturing of conductor surfaces may produce fracture surfaces that provide electrical noise generated by intermittent contact with adjacent wiring. The electrical noise may result in "over-sensing" and inappropriate delivery of defibrillation shocks with an implantable cardioverter defibrillator (ICD) lead, for example. However, in some embodiments, tantalum or tantalum-oxide structures, coatings, or layers, which have fractured, form an insulating oxide coating on the fracture surface that may serve to reduce, minimize, or eliminate electrical noise. In other embodiments, other self-healing materials (e.g., titanium, hathium, yttrium, niobium, zinc, beryllium, aluminum, zirconium, tungsten, rhenium, and their alloys and oxides, and other materials) may serve to reduce electrical noise.

In some embodiments, medical device components may be susceptible to cracking, and failure due to cracking. In such components, self-healing materials and layers of self-healing materials may be used to blunt cracks in an early phase of their development (e.g., initiation, nucleation, etc.), prior to or concurrent with crack propagation. For example, self-healing layers of in metallic conductors or polymeric insulators used in electrical leads for medical devices may fill and blunt a crack tip, reinforce an area stressed by cracking, and or fill in a cracked surface after the crack has propagated. In some embodiments, the materials may utilize conduits or channels within layers of the material to migrate liquid-forms of active matrix materials to seal the cracks (e.g., microvascular networks of passive materials containing flows of resin matrix).

According to another embodiment, the dielectric material 520 may be a composite or an organic coating that is applied over a conductor 510 made of a metal. For example, the dielectric material 520 may be formed from a nanocomposite of nanoparticles, polymer-particle or polymer-nanoparticle composites, or other materials in which an insulating entity or particle network can migrate or diffuse to damaged areas, to regenerate or re-grow materials (e.g., dielectric materials) in the damaged area. Nanoparticles or particles can be made of, for example, tantalum oxide, titanium oxide, niobium oxide, aluminum oxide, zirconium oxide, tungsten oxide, rhenium oxide, and oxides of an alloy used for the conductor 510, as discussed above. In other embodiments, nanoparticles may be embedded in layers of thermoplastic dielectric materials.

In some embodiments, the dielectric material can be made of an active composite-layered system in which layers of a passive coating matrix are alternated with layers that include an active coating component that promotes self-healing of the composite-layered system. For example, the composite-layered system may be constructed using soft lithographic and direct-write assembly methods, where the layers are printed onto a substrate in a precise arrangement producing a network of channels and conduits for active matrix material (e.g., a microvascular network). Passive layers are printed to the substrate in a layer-by-layer sequence, where active matrix material (e.g., epoxy resin, polyester, vinyl ester, etc.) is then infiltrated into the passive layers. In at least one embodiment, the conduits have approximately a 200 micrometer diameter. In other embodiments, a vascular or microvascular network with wider or narrower conduits is used. The active coating is designed to wick to cracks via capillary action and to clot the cracks or other such openings in the composite layered system (e.g., similar to coagulation of blood carried by capillaries to clot a scratch or cut of skin).

Some embodiments employing microvascular networks allow for continuous delivery of the self-healing materials (e.g., epoxy or resin matrix), providing an ability to regrow or regenerate dielectric materials in areas of the capacitor 500 (or other materials, layers, coatings, etc. used with other components of medical devices) that are repeatedly damaged. In such embodiments, a reservoir or pocket of active material may supply the microvascular channels. Additional disclosure relating to self-healing materials may be found in "Self-Healing Materials with Microvascular Networks," by K. Toohey et al. published in *Nature Materials*, volume 6, pages 581-585 in August of 2007, which is incorporated herein by reference in its entirety.

In other embodiments, a composite layer or system may include a matrix embedded with nanocontainers, providing a self-healing ability for the layer or system. In some embodiments, the nanocontainers contain active coating components for promoting self-healing. Accordingly, the nanocontainers can rupture upon application of a stimulus, thus releasing the active coating components contained by the nanocontainers. Exemplary stimuli include heat, acoustic vibration, UV light, electrical stimulation, chemical reaction, etc. In other embodiments, nanocontainers providing active materials are deposited in a material that additionally contains deposits of a catalyst that is separated from the active material by the substrate (e.g., ring-opening metathesis polymerization of dicyclopentadiene with Grubbs' catalyst, mixture of hydroxyl end-functionalized polydimethylsioxane and polydiethoxysiloxane epoxy with amine catalyst, etc.). During rupture, the active materials are released from the nanocontainers and contact the catalyst. The active materials then solidify, filling the rupture, crack, breach, etc.

In some embodiments, the nanocontainers may be designed to be at least semi-permeable to the active coating components, or the nanocontainers may be configured to release the active coating components through another method known in the art, such as those as described in "Layer-by-Layer Assembled Nanocontainers for Self-Healing Corrosion Protection," by D. Shchukin et al. published in *Advanced Materials*, volume 18, pages 1672-78 on Jun. 27, 2006, which is incorporated herein by reference in its entirety, or Self-healing Polymeric Materials: A Review of Recent Developments," by D. Wu et al. published in *Progress in Polymer Science*, volume 33 pages 479-522, which is incorporated herein by reference in its entirety, and which also provides other forms and systems of self-healing materials that may be compatible with the disclosure provided herein.

In still yet another embodiment, the dielectric material 520 can be made of any biocompatible material, including biocompatible oxides, having prescribed qualities. Specifically, dielectric materials that are both biocompatible and have a dielectric constant in the range of 1 to 100 are suitable. However particular dielectric layer thicknesses and surface areas of some embodiments vary as a function of selected materials. For example, a particular surface area and a particular layer thickness may be arranged such that their ratio is linearly proportional to a desired capacitance for the capacitor 500, where the constant of proportionality of the linear relationship just described is directly related to the dielectric constant of the selected material. In various other embodiments, dielectric strength is designed to vary as a function of the particular medical device and application (e.g., approximately 10 to 100 V DC for low-voltage applications and more than 1000 V DC for high-voltage applications).

Regeneration or re-growth of capacitor material, such as dielectric material 520, can occur during use of a medical device system. For example, voltage pulses produced when an electrode assembly is used for pacing can simultaneously affect the materials of the conductor 510 and the dielectric 520, causing these materials to migrate or diffuse. According to this example, pacing voltages can cause capacitor materials to migrate or diffuse to a damaged area, such as a damaged area 530 in a dielectric layer 520. Migrating or diffusing materials can anodize, passivate, or oxidize at the damaged area 530, causing the capacitor material to regenerate or regrow. For example, a damaged area 530, such as a scratch, can create an area of increased current density, which in turn increases the regeneration or regrowth rate of capacitor material due to anodization, passivation, or oxidation. The rate of self-healing depends upon voltage magnitude and polarity, material selection and arrangement, and a particular type and degree of damage. In some embodiments an increased voltage pulse magnitude increases the rate of self-healing.

According to a further embodiment, a medical device system can be configured so that the regeneration or re-growth rate of a self-healing capacitor material, such as a dielectric material, is controlled. For example, a pacing mode of a medical device system typically produces voltage pulses of alternating negative and positive polarity. When such pacing voltage pulses are used to migrate or diffuse capacitor materials to a damaged area, one polarity of the voltage pulses may be more useful than others due to the characteristic ionic charge of the capacitor materials. For example, a positive voltage can be used to cause capacitor materials to migrate or diffuse to a damaged area and be further anodized, passivated, or oxidized, thus regenerating or re-growing the capacitor materials. Conversely, negatively charged voltage pulses may cause little growth, no growth, or even inhibit further growth or regeneration. Therefore, a medical device system can be configured to control, for example, voltages applied to a self-healing capacitor material in order to control the regeneration or re-growth rate of the self-healing material. The same or a similar approach may be used with self-healing materials of other components of medical devices, such as insulating coatings, structural components, electrical leads, etc. that utilize an electric stimulus to initiate re-growth.

According to a further embodiment, the voltage applied to the materials of a capacitor 500 is controlled in order to control the regeneration or re-growth rate of the capacitor materials. For example, a device that controls direction of current flow, such as a diode, may be used to control the voltage that is applied to the materials of a capacitor 500. In a further example, a diode may have the attributes described in "Schottky Barrier Diodes for General Purpose Applications," a technical data publication by Agilent Technologies, which is hereby incorporated by reference in its entirety, or another commercially-available diode or electrical control system.

FIG. 12 shows an embodiment of a configuration used for controlling the regeneration or re-growth rate of a damaged area 530 of a capacitor 500. A device 604 to control the direction of current flow can be used and arranged so that positive voltage pulses can be applied to the capacitor 500 during pacing, thus fostering regeneration and re-growth of capacitor material. The current flow control device 604 can be a diode, such as in the example of FIG. 12, or another device configured to control the flow of current.

According to an exemplary embodiment, the current flow control device 604 is further configured to control the direction of current flow so that negative voltage pulses are blocked and not applied to the capacitor materials. By blocking negative voltage pulses, the current control device 604 can be configured to promote the regeneration or re-growth of self-healing capacitor materials. As described, the self-healing materials heal when positive voltage pulses are applied. Accordingly, negative voltage pulses, which may inhibit regeneration or re-growth, are not applied to the self-healing capacitor material. As shown in the example of FIG. 12, the current flow control device 604 can be connected between the capacitor 500 and the tip electrode 207. Furthermore, the device 604 can be configured so that the device 604 has a low impedance to RF currents induced during MRI, but a high impedance to a selected voltage pulse polarity during a pacing operation of a medical device system. According to another embodiment, the current flow control device 604 is configured to permit application of negative voltage pulses to capacitor materials and to block positive voltage pulses.

According to an exemplary embodiment, the current flow control device 604 is configured to have a sufficient reverse bias voltage rating to withstand a potential of a voltage pulse that the device 604 is configured to block, according to a further embodiment. For example, the current flow control device 604 should have a reverse bias voltage rating of at least approximately 10V (i.e., if the potential of a blocked pulse is 10V). In another example, the current flow control device 604 should have a reverse bias voltage rating of at least approximately 20V.

According to an exemplary embodiment, the current flow control device 604 can also be configured so that the forward bias voltage rating is at a minimum in order to permit maximum transfer of current when the voltage pulse that the device 604 is configured to pass is applied. For example, the forward voltage rating of the device can be approximately 0.41V. In another example, the forward voltage rating of the device can be approximately 150 mV.

According to an exemplary embodiment, the wattage rating of the current flow control device 604 should be sufficient to withstand the current conducted by the device 604. For example, the device 604 can have a wattage rating of approximately 100 mW. In another example, the device 604 can have a wattage rating of approximately 250 mW. Furthermore, a device 604 can have combinations of these rating values.

In other embodiments, stimuli other than (or in combination with) electrical pulses are used to controllably regenerate or promote re-growth (e.g., filling of cracks, etc.). For example, some stimuli and catalysts include temperature (e.g., heat), UV light (or electromagnetic radiation), acoustic vibration, release or contact with embedded substances (e.g., catalyst), fatigue loading, tensile, shear or compressive stress or pressure, etc. For example in some embodiments, implanted medical devices may fill or repair cracks as a result of repeated compressive forces, such as repeated or sustained pressing of sidewalls of a crack together. In other embodiments, a region of lower pressure in a self-healing material, such as an area surrounding a gouge in a multvascular network, may induce migration of resin (or other migrating or diffusing materials) to fill the gouge. In still other embodiments, UV light may be applied to the implanted material, such as a dental implant, to regrow or self-heal materials serving as a biocompatible insulator, protective coating, decorative facade layer, etc.

Figure 13A:
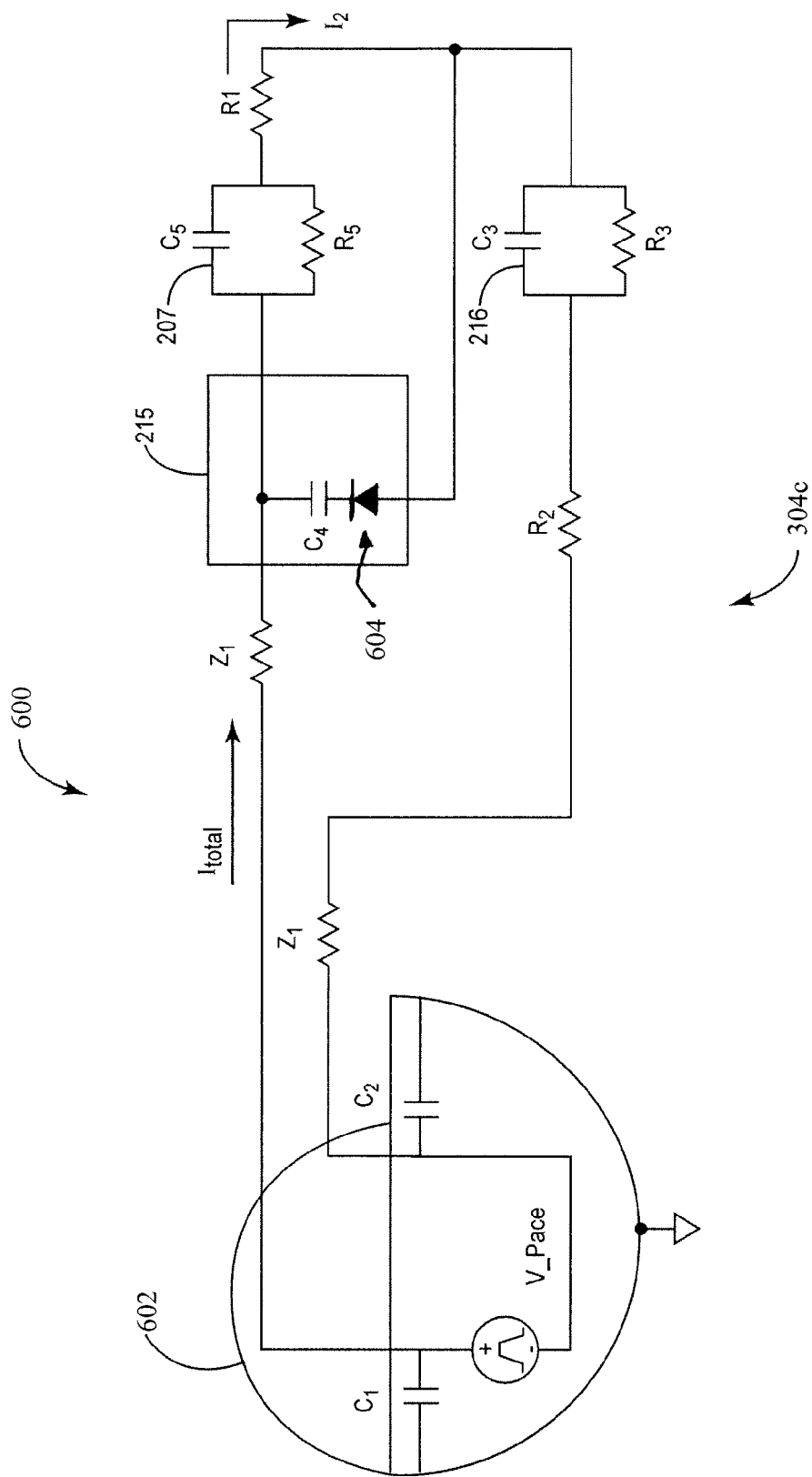
FIG. 13A is a schematic bipolar circuit for a simplified medical device system containing a capacitor and diode arrangement.
Figure 13B:
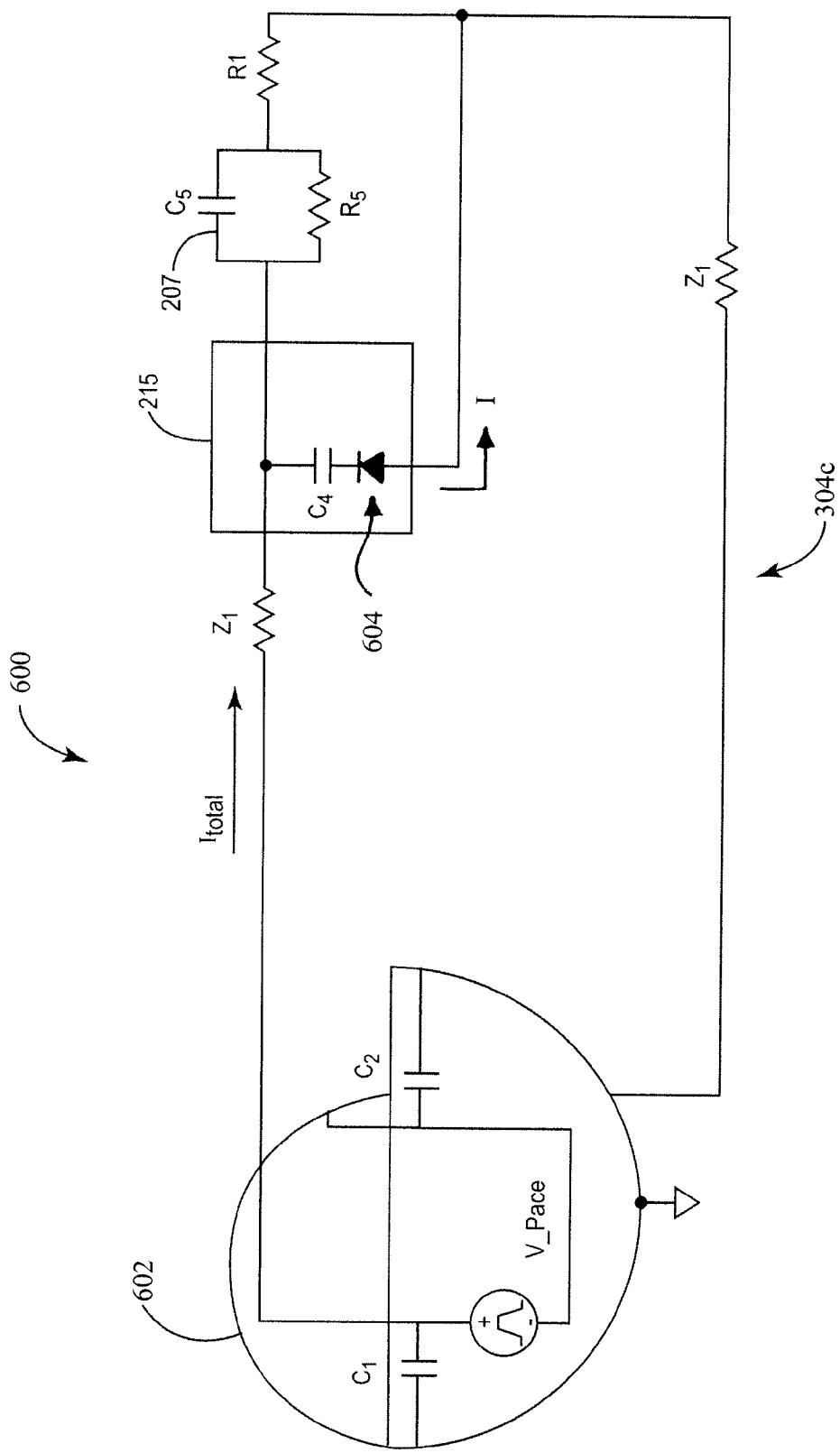
FIG. 13B is a schematic unipolar circuit for a simplified medical device system containing a capacitor and diode arrangement.

FIGS. 13A and 13B depict another embodiment that includes a simplified circuit 600 for a medical device system during pacing and MRI conditions, respectively. Circuit 600 includes an IMD circuit 602 (e.g. a pacemaker circuit, neurostimulator circuit etc.) and a bipolar shunted lead 304c. Circuit 600 includes the same elements as circuit 300 depicted in FIGS. 9A-9B, except that the magnetostrictive element 215 and the capacitor (C4) are further coupled to a current flow control device 604. As in the examples of FIGS. 9A and 9B, high frequency signals (i.e. from the MRI) pass to C4, causing currents produced by the high frequency signals to short C4 and bypass the tip electrode 207. Conversely, low frequency signals pass to and from tip electrode 207. C4 is shorted when exposed to high frequency signals, as shown by current I in FIG. 9B (see also FIG. 13B). C4 acts as an "open circuit" when exposed to low frequency signals, which causes the current $I_2$ of pacing pulses to pass directly to tip electrode 207, as shown FIG. 9A (see also FIG. 13A). Furthermore, current flow control device 604 controls the polarity of voltage that is applied to capacitor C4, thus controlling the rate of regeneration or re-growth of capacitor material, as described in any of the embodiments above.

It is understood that the present invention is not limited for use in pacemakers, cardioverters of defibrillators. Other uses of the innovations described herein may include uses in patient monitoring devices, or devices that integrate monitoring and stimulation features, such as INS devices. In those cases, the leads may include sensors disposed on distal ends of the respective lead for sensing patient conditions.

The leads described herein may be used with a neurological device such as a deep-brain stimulation device or a spinal cord stimulation device. In those cases, the leads may be stereotactically probed into the brain to position electrodes for deep-brain stimulation, or into the spine for spinal stimulation. In other applications, the leads described herein may provide muscular stimulation therapy, gastric system stimulation, nerve stimulation, lower colon stimulation, drug or beneficial agent dispensing, recording or monitoring, gene therapy, or the like. In short, the leads described herein may find useful applications in a wide variety medical devices that implement leads and circuitry coupled to the leads.

Various embodiments of the invention have been described. These and other embodiments are within the scope of the following claims. For example, electrode 207 may include variously shaped electrodes such as ring shaped or other suitable shapes. Additionally, skilled artisans appreciate that other dimensions may be used for the mechanical and electrical elements described herein.

What is claimed is:

1. A medical device system comprising:
   a medical device configured to deliver electrical stimulation to a patient;
   a lead electrically connected to the medical device, the lead comprising at least one electrode assembly, wherein the at least one electrode assembly comprises:
   an electrode, and
   a shunted lead circuit with a self-healing material integrated onto a surface of at least a portion of the lead, wherein the medical device is configured to control a regeneration rate of the self-healing material by at least controlling a stimulus applied to the self-healing material.

2. The medical device system of claim 1, wherein the stimulus comprises a voltage, the medical device system further comprising a current flow control device adapted to control the regeneration rate of the self-healing material by controlling the voltage applied to the self-healing material.

3. The medical device system of claim 2, wherein the current flow control device comprises a diode.

4. The medical device system of claim 2, wherein the current flow control device is configured to block voltages of negative polarity.

5. The medical device system of claim 2, wherein the current flow control device is configured to block voltages of positive polarity.

6. The medical device system of claim 3, wherein the diode has a reverse bias voltage rating of at least approximately 10 Volts (V).

7. The medical device system of claim 3, wherein the diode has a forward bias voltage rating of approximately 0.41 Volts (V) and a wattage rating of approximately 100 milliWatts (mW).

8. The medical device system of claim 3, wherein the diode has a reverse bias voltage of at least approximately 20 Volts (V), a forward bias voltage rating of approximately 150 milliVolts (mV), and a wattage rating of approximately 250 milliWatts (mW).

9. The medical device system of claim 1, wherein the stimulus comprises at least one of heat, an acoustic vibration, ultra-violet (UV) light, an electrical stimulus, or a chemical stimulus.

10. The medical device system of claim 1, wherein the stimulus comprises a voltage, and wherein the medical device is configured to increase the regeneration rate of the self-healing material by increasing a magnitude of the voltage.

11. A medical device system comprising:
    an implantable medical device having a housing adapted to be implanted within a body of a patient;
    an electrical lead coupled to the implantable medical device, wherein the lead is configured to at least one of sense electrical activity of an organ of the patient or deliver electrical stimulation to the organ of the patient; and
    a self-healing material coupled to at least one of the implantable medical device or the electrical lead, wherein the self-healing material is configured to repair a breach while implanted within the body of the patent, and wherein the implantable medical device is configured to control a regeneration rate of the self-healing material by at least controlling a stimulus applied to the self-healing material.

12. The medical device system of claim 11, wherein at least one of the implantable medical device or the electrical lead comprises a capacitor, and wherein the self-healing material forms at least one of a dielectric layer or a conductive layer of the capacitor.

13. The medical device system of claim 11, wherein the self-healing material is configured to repair the breach via at least one of anodization, passivation, or oxidation.

14. The medical device system of claim 11, wherein the self-healing material comprises at least one of tantalum oxide, titanium oxide, hafnium oxide, yttrium oxide, zinc oxide, beryllium oxide, niobium oxide, aluminum oxide, zirconium oxide, tungsten oxide, or rhenium oxide.

15. The medical device system of claim 11, wherein the self-healing material comprises at least one of tantalum or tantalum oxide.

16. The medical device system of claim 11, wherein the self-healing material comprises an active matrix material, and wherein the active matrix material is configured to repair the breach by at least diffusing to the breach.

17. The medical device system of claim 16, wherein the active matrix material is configured to diffuse to the breach through a microvascular network.

18. The medical device system of claim 11, wherein the self-healing material comprises at least one of organic nanoparticles, inorganic nanoparticles, polymer-particles, or nanoparticle composites.

19. A medical device system according to claim 11, wherein the self-healing material comprises a composite comprising layers of a passive coating matrix alternated with layers of an active coating component, wherein the active coating component is configured to promote repair of the self-healing material.

20. A medical device system according to claim 11, wherein the self-healing material comprises a matrix embedded with nanocontainers containing active coating components configured to promote repair of the self-healing material.

21. The medical device system of claim 11, wherein the stimulus comprises a voltage, the medical device system further comprising a current flow control device adapted to control the regeneration rate of the self-healing material by controlling the voltage applied to the self-healing material.

22. The medical device system of claim 21, wherein the current control flow device comprises a diode.

23. The medical device system of claim 21, wherein the current flow control device is configured to block voltages of negative polarity.

24. The medical device system of claim 21, wherein the current flow control device is configured to block voltages of positive polarity.

25. The medical device system of claim 11, wherein the housing comprises the self-healing material, and wherein the self-healing material is biocompatible.

26. The medical device system of claim 11, wherein the stimulus comprises at least one of heat, an acoustic vibration, ultra-violet (UV) light, an electrical stimulus, or a chemical stimulus.

27. The medical device system of claim 11, wherein the stimulus comprises a voltage, and wherein the implantable medical device is configured to increase the regeneration rate of the self-healing material by increasing a magnitude of the voltage.

28. A method for making a medical device system having regenerative capabilities, the method comprising:
    electrically connecting an electrical lead to an implantable medical device, wherein the implantable medical device is adapted to be implanted within a body of a patient,
    wherein the electrical lead is adapted to at least one of sense electrical activity of an organ of the patient or deliver electrical stimulation to the organ of the patient,
    wherein electrically connecting the implantable medical device to the electrical lead
    comprises electrically connecting the implantable medical device to the electrical lead via an electrical circuit, wherein the electrical circuit comprises a self-healing material that is configured to be regenerated while implanted within the body of the patient, and wherein the implantable medical device is configured to control a regeneration rate of the self-healing material by at least controlling a stimulus applied to the self-healing material.

29. The method of claim 28, wherein the self-healing material is configured to be regenerated by at least one of anodization, passivation, or oxidation.

30. The method of claim 28, wherein the self-healing material comprises an active matrix material, and wherein the self-healing material is configured to be regenerated by at least diffusion of the active matrix material to a damaged area.

31. The method of claim 30, wherein the active matrix material is configured to diffuse to the damaged area through a microvascular network, and wherein the self-healing material is configured to be repeatedly regenerated.

32. The method of claim 28, wherein the stimulus comprises at least one of heat, an acoustic vibration, ultra-violet (UV) light, an electrical stimulus, or a chemical stimulus.

33. The method of claim 28, wherein the stimulus comprises a voltage, and wherein the medical device is configured to increase the regeneration rate of the self-healing material by increasing a magnitude of the voltage.

34. A method for using a medical device system having regenerative capabilities, the method comprising:
    delivering electrical stimulation from a medical device to an organ of a patient via an electrical lead,
    wherein the medical device system comprises the electrical lead, the medical device, and an electrical circuit electrically connecting the medical device and the electrical lead,
    wherein the electrical circuit comprises a self-healing material that is configured to be regenerated while implanted within a body of the patient, and
    wherein the medical device controls a regeneration rate of the self-healing material by at least controlling a stimulus applied to the self-healing material.

35. The method of claim 34, wherein the self-healing material is configured to be regenerated by at least one of anodization, passivation, or oxidation.

36. The method of claim 34, wherein the self-healing material comprises an active matrix material, and wherein the self-healing material is configured to be regenerated by at least diffusion of the active matrix material to a damaged area through a microvascular network, and wherein the self-healing material is configured to be repeatedly regenerated.

37. The method of claim 34, wherein the stimulus comprises at least one of heat, an acoustic vibration, ultra-violet (UV) light, an electrical stimulus, or a chemical stimulus.

38. The method of claim 34, wherein the stimulus comprises a voltage, and wherein the medical device increases the regeneration rate of the self-healing material by increasing a magnitude of the voltage.

* * * * *

UNITED STATES PATENT AND TRADEMARK OFFICE
CERTIFICATE OF CORRECTION

| | | |
|---|---|---|
| PATENT NO. | : 8,442,651 B2 | Page 1 of 1 |
| APPLICATION NO. | : 12/718897 | |
| DATED | : May 14, 2013 | |
| INVENTOR(S) | : Gonzalo Martinez et al. | |

It is certified that error appears in the above-identified patent and that said Letters Patent is hereby corrected as shown below:

In the Claims

Col. 18, line 23, delete "patent" and insert in place thereof -- patient --.

Signed and Sealed this
Sixth Day of August, 2013

Teresa Stanek Rea
*Acting Director of the United States Patent and Trademark Office*